US012708465B2

(12) United States Patent
Fitzsimons et al.

(10) Patent No.: US 12,708,465 B2
(45) Date of Patent: Aug. 18, 2026

(54) COLLABORATIVE SURGICAL ROBOTIC PLATFORM FOR AUTONOMOUS TASK EXECUTION

(71) Applicant: SEVA ROBOTICS LLC, Lilburn, GA (US)

(72) Inventors: Philip Matthew Fitzsimons, Lilburn, GA (US); Angad Singh, Marietta, GA (US)

(73) Assignee: SEVA ROBOTICS LLC, Lilburn, GA (US)

( * ) Notice: Subject to any disclaimer, the term of this patent is extended or adjusted under 35 U.S.C. 154(b) by 322 days.

(21) Appl. No.: 17/997,412

(22) PCT Filed: Apr. 29, 2021

(86) PCT No.: PCT/US2021/029892
§ 371 (c)(1),
(2) Date: Oct. 28, 2022

(87) PCT Pub. No.: WO2021/222564
PCT Pub. Date: Nov. 4, 2021

(65) Prior Publication Data
US 2023/0165649 A1 Jun. 1, 2023

Related U.S. Application Data

(60) Provisional application No. 63/026,181, filed on May 18, 2020, provisional application No. 63/017,248, filed on Apr. 29, 2020.

(51) Int. Cl.
*A61B 34/32* (2016.01)
*A61B 34/10* (2016.01)
(Continued)

(52) U.S. Cl.
CPC .............. *A61B 34/32* (2016.02); *A61B 34/10* (2016.02); *A61B 34/20* (2016.02);
(Continued)

(58) Field of Classification Search
CPC ......... A61B 34/32; A61B 34/10; A61B 34/20; A61B 2034/107; A61B 2034/2048;
(Continued)

(56) References Cited

U.S. PATENT DOCUMENTS 11,457,984 B1 * 10/2022 Allford .............. A61B 17/1675
2011/0015649 A1 * 1/2011 Anvari .................. A61B 34/20 606/130
(Continued)

OTHER PUBLICATIONS

Extended European Search Report for European Patent Application No. 21797016.9 dated Sep. 21, 2023, 8 pages.

*Primary Examiner* — Dylan M Katz
(74) *Attorney, Agent, or Firm* — McDonald Hopkins LLC

(57) ABSTRACT

Systems and methods for controlling a robotic device to perform a tissue modification task are disclosed. The methods include receiving a task plan relative to a patient's image data. The task plan includes information relating to an entry point of a surgical tool into a tissue and a planned trajectory of the surgical tool inside the tissue for performing the tissue modification task. The methods also include controlling the robotic device to autonomously or semi-autonomously execute the tissue modification task by identifying datum point as the entry point of the surgical tool into the tissue, activating the surgical tool to perform the tissue modification task along the planned trajectory from the datum point, determining whether the surgical tool has reached an end of the planned trajectory, and retracting the surgical tool from the tissue upon determining that the surgical tool has reached the end of the planned trajectory.

28 Claims, 9 Drawing Sheets

(51) Int. Cl.
*A61B 34/20* (2016.01)
*A61B 90/00* (2016.01)

(52) U.S. Cl.
CPC . *A61B 2034/107* (2016.02); *A61B 2034/2048* (2016.02); *A61B 2034/2059* (2016.02); *A61B 2034/2065* (2016.02); *A61B 2090/064* (2016.02)

(58) Field of Classification Search
CPC .... A61B 2034/2059; A61B 2034/2065; A61B 2090/064; A61B 2017/00725; A61B 2090/365; A61B 34/30
See application file for complete search history.

(56) References Cited

U.S. PATENT DOCUMENTS

| | | | | |
|---|---|---|---|---|
| 2015/0366157 | A1* | 12/2015 | Holmstrom | B25J 9/1664<br>119/670 |
| 2018/0049822 | A1* | 2/2018 | Henderson | A61B 34/76 |
| 2018/0085135 | A1 | 3/2018 | Singh et al. | |
| 2018/0200002 | A1* | 7/2018 | Kostrzewski | A61B 34/25 |
| 2018/0325608 | A1 | 11/2018 | Kang et al. | |
| 2019/0008599 | A1* | 1/2019 | Lynch | A61B 17/00234 |
| 2019/0090966 | A1* | 3/2019 | Kang | A61B 17/1671 |

* cited by examiner

COLLABORATIVE SURGICAL ROBOTIC PLATFORM FOR AUTONOMOUS TASK EXECUTION

CROSS-REFERENCE TO RELATED APPLICATIONS

This application is a U.S. National Phase Application of PCT International Application No. PCT/US2021/029892, filed Apr. 29, 2021 and entitled "COLLABORATIVE SURGICAL ROBOTIC PLATFORM FOR AUTONOMOUS TASK EXECUTION" which claims priority to U.S. provisional patent application No. 63/017,248 filed Apr. 29, 2020 and entitled "SYSTEMS AND METHODS FOR A SURGICAL ROBOTIC PLATFORM FOR AUTONOMOUS TASK EXECUTION" and U.S. provisional patent application No. 63/026,181 filed on May 18, 2020 entitled "SYSTEMS AND METHODS FOR A COLLABORATIVE ROBOTIC PLATFORM FOR AUTONOMOUS TASK EXECUTION." The contents of each of the priority documents are expressly incorporated herein by reference in their entirety.

TECHNICAL FIELD

The present disclosure relates generally to systems and methods for robotic surgery, and more particularly provides a collaborative robotic platform for autonomous or semi-autonomous execution of surgical tasks involving modification of hard tissue (e.g. bone) in procedures such as those of the musculoskeletal system.

BACKGROUND

Several commercial surgical robotic platforms currently exist that include a master-slave system. Specifically, the surgeon typically operates a master controller to remotely control the motion of surgical instruments at the surgical site. The controller may be separated from the patient by a significant distance (e.g., across the operating room, in a different room, or in a completely different building than the patient). Alternatively, a controller may be positioned quite near the patient in the operating room. Regardless, the controller will typically include one or more hand input devices (such as joysticks, exoskeletal gloves, master manipulators, or the like) which are coupled by a servo mechanism to the surgical instrument. More specifically, servo motors move a manipulator or "slave" supporting the surgical instrument based on the surgeon's manipulation of the hand input devices. During an operation, the surgeon may employ, via the robotic surgery system, a variety of surgical instruments such as tissue graspers, needle drivers, electrosurgical cautery probes, etc. Each of these structures performs functions for the surgeon, for example, holding or driving a needle, grasping a blood vessel, or dissecting, cauterizing, or coagulating tissue. One such robotic platform is the Da Vinci robot developed by Intuitive Surgical that is a master-slave system that simply scales down the motion of the surgeon and has no real autonomy. It is, therefore, not a robot in the truest sense of the word. Additionally, the Da Vinci system is mostly limited to soft tissue microsurgery and not suited to musculoskeletal procedures involving hard tissue.

Other commercial systems such as the MAKO (Stryker, USA) designed for certain musculoskeletal procedures such as knee, hip, and spine surgeries, guide the surgeon via physical guides or haptic feedback but still lack the ability to autonomously execute tasks. The TSolution-One (previously ROBODOC; Think Surgical, USA) provides limited autonomy but is designed for a specific task (knee cutting) in knee surgery and is not a generalized solution for the variety of tasks that are encountered in musculoskeletal surgery such as drilling, burring, cutting, and reaming of different types of hard tissue such as hips, spine, shoulder, elbow, ankle, jaw, and the cranium. It also relies on cumbersome bone monitoring and registration processes that are prone to error and add time to the procedure.

Specifically, as more and more different surgical tools and tasks are provided for use with a robotic system, the differences between the tool structures (and the interaction between the tool and the other components of the robotic system) become more pronounced. For example, the desired and/or practicable ranges of motion for a drill may be significantly different than those of a cutting saw, for example. As such, even after a tool is properly placed, the time involved in reconfiguring the robotic system to take advantage of a different tool may add significantly to the total tool change delay and cost.

Existing robotic platforms also typically have cumbersome and inefficient image registration and bone monitoring workflows that in many cases are exacerbated by use of large optical tracking systems that have line-of-sight issues. In addition, systems cost well over $1million. For the above reasons, current surgical robotic systems generally provide poor value that makes it hard for surgeons and hospital administrators to justify the large dollar investments. This has limited the spread of robotic technology especially in smaller ambulatory surgery centers and resource limited regions of the world.

This document describes methods and systems that are directed to addressing the problems described above, and/or other issues.

SUMMARY

In one or more scenarios, systems and methods for controlling a robotic device to perform a tissue modification task are disclosed. The systems may include a robotic device that includes surgical tool, a processor, and a non-transitory computer readable medium. The non-transitory computer readable medium includes one or more programming instructions that when executed by the processor will cause the processor to execute the methods of this disclosure. The methods may include receiving a task plan and using the task plan for controlling the robotic device to, autonomously or semi-autonomously, execute the tissue modification task. The task plan may include information relating to an entry point of a surgical tool into a tissue and a planned trajectory of the surgical tool inside the tissue for performing the tissue modification task, and may be relative to a patient's image data. Controlling the robotic device to execute the tissue modification task may include identifying a first datum point as the entry point of the surgical tool into the tissue, activating the surgical tool to perform the tissue modification task along the planned trajectory when the surgical tool is positioned at the first datum point, determining if the surgical tool has reached an end of the planned trajectory, and retracting the surgical tool from the tissue when the surgical tool has reached the end of the planned trajectory. The first datum point may be identified when a force applicable on the surgical tool when positioned at the first datum point is greater than a first threshold value. Optionally, the determination of whether the surgical tool has reached an end of the planned trajectory may be based on at least the force measurements on the surgical tool and/or a position of the tool along the planned trajectory.

In certain implementations, the methods may also include displaying the surgical tool position in relation to the patient's image data and the planned trajectory in real-time on, for example, a display device.

In some implementations, the methods may further include controlling the robotic device to position the surgical tool at a pre-entry position that is within a threshold distance of the entry point and at an angle of entry into the tissue. Optionally, the robotic device may be controlled to incrementally move the surgical tool from the pre-entry position towards the entry point until the surgical tool reaches the first datum point, and to force applicable on the surgical tool at each such incremental position may be measured.

In some other implementations, the methods may also include continuously monitoring a force applicable on the surgical tool while performing the tissue modification task. Such continuous monitoring may include subtracting a reference force (e.g., a gravitational force) from a measured force. Additionally and/or alternatively, the methods may include, upon activation of the surgical tool, controlling the robotic device to position the surgical tool at a first incremental position along the planned trajectory to perform the tissue modification task, determining whether the force applicable has become less than a second threshold at the first incremental position, and controlling the robotic device to position the surgical tool at a second incremental position along the planned trajectory to perform the tissue modification task if the force applicable has become less than the second threshold value. However, while the force applicable is not greater than the second threshold value, the methods may include continuing the monitoring of the force applicable on the surgical tool while performing the surgical task until expiration of a first time period indicative of a risk. Optionally, when the force applicable exceeds a third threshold value the methods may include transmitting an alert to a user. In various implementations, the methods may include determining the first threshold value, the second threshold value, and the third threshold value based on at least an estimated stiffness of the tissue.

In certain scenarios, the methods may also include controlling the robotic device to abort the tissue modification task in respond to determining that a search limit has been exceeded prior to identification of the datum point. The search limits may be related to time, distance, and/or number of attempts.

In certain other scenarios, the methods may include determining a spatial relationship between a first coordinate frame of the task plan and a second coordinate frame of the robotic device, and transforming the task plan relative to the patient's image data to the second coordinate frame of the robotic device. Such spatial relationship may be determined by identifying a plurality of registration points on the tissue surface (when the robotic device in a hand-guidance mode), and mapping the plurality of registration points to the patient's image data. The plurality of registration points on the tissue surface may be identified by attaching a registration tool to the robotic device, monitoring applicable force on the registration tool while the registration tool is contacted with a plurality of points over the tissue surface in the hand-guidance mode, and identifying one or more positions of the registration tool as registration points when the monitored applicable force is greater than a contact threshold value. Optionally, such methods may also include performing segmentation of three-dimensional surface information of the tissue collected by a vision system to identify a second plurality of registration points proximate to the one or more of the plurality of registration points, where the segmentation is performed based on one or more of the plurality of registration points.

Optionally, receiving the task plan may include receiving the task plan from a user by user-guided contact of the surgical tool with the patient's anatomy and at least one user-specified plan parameter.

BRIEF DESCRIPTION OF THE DRAWINGS

The components in the drawings are not necessarily to scale relative to each other. Like reference numerals designate corresponding parts throughout the several views.

DETAILED DESCRIPTION

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to." Definitions for additional terms that are relevant to this document are included at the end of this Detailed Description.

As discussed above, current robotic surgical systems are not autonomous, not easily configurable for different types of surgical tasks for manipulation of hard tissue, have cumbersome registration and/or bone monitoring workflows, and/or rely on expensive optical trackers. The current disclosure is aimed at providing a surgical robotic platform capable of performing common surgical tasks involving modification of hard tissue autonomously or semi-autonomously under human supervision and/or control, and methods of use thereof. The disclosure provides generalized systems and methods for hard tissue procedures (or surgical tasks) with a streamlined workflow including planning of the surgical task, registration, and execution. The cost-effectiveness, utility, and ease of use of such a system may spur mass adoption of robotics in musculoskeletal procedures thereby improving access to and quality of the surgical procedure.

Examples of such surgical tasks may include, without limitation, drilling, burring, cutting, reaming, ablation, tapping, etc. of hard tissue such as bones and cartilage, placement of hardware such as screws and pin in the tissue, or the like. Example surgical procedures where such tasks are performed are surgeries performed for the treatment of musculoskeletal trauma, degenerative diseases, and/or deformity such as in knees, hips, spine, shoulder, elbow, ankle, jaw, cranium, teeth, or the like. It will be understood to those of skill in the art that while the current disclosure describes surgical tasks performed on hard tissue, the disclosure is not so limiting. The disclosed system and methods provide a means to perform one or more of the above mentioned tasks autonomously or semi-autonomously under human supervision and/or control (as described below).

Figure 1:
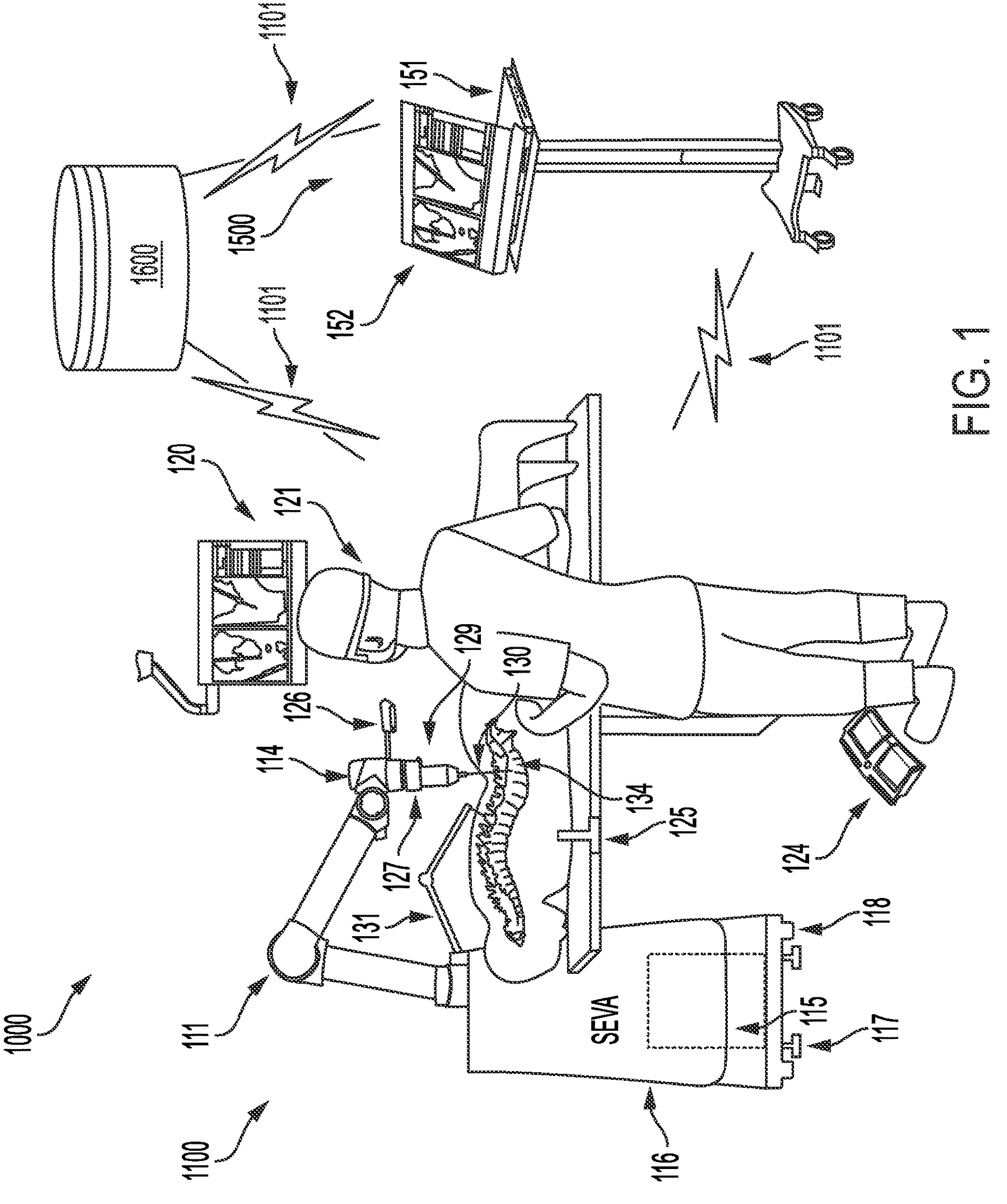
FIG. 1 is a schematic diagram illustrating an example collaborative robotic system for performing surgical tasks involving modification of hard tissue.

FIG. 1 provides a schematic diagram of an example robotic system for performing surgical tasks such as modification and/or manipulation of hard tissue autonomously or semi-autonomously under human supervision and/or control. As shown in FIG. 1, the robotic system 1000 may include two sub-systems—a local sub-system 1100 (also referred to as the "surgical robot" or "robot"), a remote sub-system 1500, and data store(s) 1600 in communication with each other over network 1101. Data store(s) 1600 may be any kind of data store such as, without limitation, patient data store(s), task plan data store(s), user information data store(s), surgical tool information data store(s), robotic device information data store(s), or any other type of content data store(s). Network 1101 may be any type of network such as a local area network (LAN), a wide area network (WAN) such as the Internet, a cellular network, a satellite network, or a combination thereof, and may be wired or wireless. Communication protocols may leverage current and future security, authentication, and encryption technologies.

The local sub-system 1100 is placed in close proximity to the patient and executes and/or assists with the execution of one or more surgical tasks. The remote sub-system 1500 is communicatively coupled to the local sub-system 1100 over network 1101, and may perform surgical task planning on acquired patient image data, spatial registration, and/or display of data before, during, and/or after task execution. The remote sub-system 1500 may also be configured for monitoring, supervision, and/or control of the task being performed by the local sub-system 1100. Since the remote and local sub-systems are capable of being communicatively coupled one or more processes may be shared between the two sub-systems and/or may be performed at either system. As such, while the disclosure may describe a certain process as being performed at the remote or the local sub-system, it is not so limiting. Furthermore, the word "remote" herein is meant to convey flexibility in the location of sub-system 1500 and can be any location whether in close proximity to the patient or in a faraway location e.g. offsite, in a different city or different country or anywhere in between. For example, in some use cases remote sub-system 1500 may be in close proximity to the patient (e.g., in the same room) and placed according to surgeon preference or specifics of the use case. However, the disclosure allows for sub-system 1500 to be configured for placement at a wide variety of locations locally or globally. It is anticipated that the remote sub-system 1500 will not need to be communicatively coupled to the local sub-system 1100 for certain tasks that do not require information collected using sub-system such as pre-surgical planning on image date. Various components or subsystems of the system 1000 (e.g., the local sub-system 1100 and the remote sub-system 1500) may be embodied in processor hardware and computer-readable programming instructions. Specific components within such systems and sub-systems will be described in the discussion of FIG. 9 later in this document.

As shown in FIG. 1, a local sub-system (i.e., the robot) 1100 may include a robotic arm 111 with sufficient degrees of freedom to allow it to move in one or more directions (translational and/or rotational) in order to deliver a medical instrument, such as a surgical tool 129 (which may be procedure-specific) to an appropriate location relative to a patient's body. The surgical tool 129 may form the end effector of the robotic arm 111. For example, as shown in FIG. 1, the robotic arm 111 may be positioned proximate to the patient's spine 134 and manipulated to access the spine. In various embodiments, movement of the robotic arm 111 that may comprise two or more linkages may be controlled via one or more actuators and encoders. The robotic arm 111 may also include a wrist 114 that can permanently and/or removably couple with a force torque sensor 127, a variety of surgical tools 129 (e.g., a power tool, drill, etc.), a vision system comprising at least one camera 126, and/or other components required for execution of the surgical task, using any now or hereafter known coupling mechanisms. While FIG. 1 shows a single robotic arm 111, the local-subsystem 1100 may include any number of robotic arms that may include similar or dissimilar components coupled to the wrist.

In various implementations, the robotic arm 111 may be mounted on a base 116. The base 116 may be stationary and stabilized on the floor using any now or hereafter known stabilization mechanisms know in the art (such as feet 117) that may, optionally, be controlled to engage and/or disengage with a surface (e.g., the floor). Additionally and/or alternatively, the base may be mobile (e.g., using casters 118, wheels, etc.) and may appropriately position the robotic arm 111 with respect a patient. In certain embodiments, the mobile base may be a manually movable base that rolls on casters 118 and/or may be an automated or semi-automated vehicle. In other embodiments, the base 116 may be secured to the operating table or be of small enough form factor to be mounted on a rail of the operating table. The base 116 may also be designed and configured to accommodate and secure computing device 115 and control circuitry for any other robot peripherals. It may also accommodate cooling fans and other such devices for thermal management, one or more power supplies and back up batteries, or other components.

As discussed above, the local sub-system 1100 can, optionally, include a vision system capable of collecting information about the shape, position, and/or appearance of surfaces. Such a vision system may comprise one or more imaging devices (e.g., cameras 126) and/or associated image processing software that may run on one or more computing devices embedded in the camera or on external computing devices in the local-subsystem 1100 and/or remote sub-system 1500. For example, the camera 126 may be coupled to and/or mounted on the wrist 114 as shown in FIG. 1. However, the disclosure is not so limiting and the camera may be included at any other suitable location on the local sub-system 1100 and/or at a location that is not on the local sub-system that provide an unobstructed view of the surgical field such as on a boom attached to a movable cart, or integrated into or attached to one or more surgical lights, or the like (in such locations the camera may be in communication with the local sub-system 1100 and/or the remote sub-system 1500). The vision system may be configured such that the spatial relationship between its coordinate frame and the robot coordinate frame is known or derivable using techniques well known in the art. An example technique known in the art is the hand-eye calibration technique.

The vision system may be configured for, without limitation, to collect information about the shape, position, and/or appearance of surfaces which may include detecting and measuring points on the surface, identifying the surfaces and/or objects (generally, referred to as objects), and tracking the above information in real-time or near real-time. The surface and/or object detection, identification, and/or tracking can be performed using any now or hereafter known algorithms including, without limitation, human coded algorithms, artificial intelligence (AI)-based machine learning algorithms or some combination thereof. Furthermore, while the disclosure teaches the use of a vision system, other sensor systems such as ultrasound probes, x-ray acoustic probes, photo acoustic probes, or laser based sensors (e.g LIDAR), radio frequency based sensors, magnetic resonance imaging (MRI) based systems, etc. may be used without deviating from the principles of this disclosure. Some of the above sensor systems may require contact with the anatomy of a patient which can be achieved by proper selection of the attachment mechanism to wrist 114.

An example vision system may include a RGB-D camera 126 and image processing software to capture color and depth information and generate three dimensional (3D) position, shape, and RGB color information of a surface and/or an object. An example of such a vision system is the Structure Sensor and associated image processing software from Occipital USA or the RealSense camera and associated software from Intel USA. In such vision systems information from RGB-D cameras may be processed to generate a surface scan comprising 3D point clouds, depth maps and/or color maps of the anatomy of interest such as spine 134 and surrounding tissue which can be used for registration (as will be described later), obstacle avoidance, and path planning for performing a surgical task. Some RGB-D cameras rely on the texture of the surface for depth information and such texture can be supplemented and/or augmented with external light projectors, typically operating in the infra-red (IR) spectrum, to increase the accuracy of the depth information. Alternatively and/or additionally, one or more of the cameras 126 could be multi-spectral camera such as the SpectroCam Multispectral camera from OceanInsight, FL.

In certain embodiments, to aid the vision system in detecting, identifying and/or tracking the objects of interest (such as a patient, patient anatomical feature, tool, arm, or the robot, etc.), such objects may be rigidly coupled to fiducials that can be easily detected and identified by the cameras (or other sensors). An example of a vision system that tracks fiducials is the Polaris Vega System from NDI medical, Canada that utilizes infra-red illumination, and one or more infra-red cameras 126 to detect fiducials equipped with reflector balls. The vision system may also be communicatively coupled to remote sub-system 1500 to transfer information for registration and/or images for display.

As previously mentioned, robotic arm 111 of the local sub-system 1100 may include a wrist link 114. Wrist 114 may be configured to couple to and/or include a force torque sensor 127 and that is positioned between the wrist 114 and tool 129 such that the force torque sensor 127 can measure various forces and torques applicable on the tool or as applied by a user. One or more other force sensors may also be included in various joints, linkages, or other positions of the robotic arm 111. While forces and torques are different physical parameters, they both generally involve forces and will be referred to collectively as "force" hereafter. An example force sensor suitable for use in the disclosed invention is the Axia 80-M20 F/T sensor from ATI Industrial Automation NC.

Tool 129 can be one or more of a variety of unpowered and powered surgical tools such as a rotary drill, burr tool, reciprocating saw, pin or screw drivers, ultrasonic scalpel/drill/driver, chisels, etc. that are commonly used in musculoskeletal surgical procedures. Such tools may include a shaft 130, optionally, including a working end or surface such as a tip, sharp edge, and/or other tissue manipulator surface/end that interacts with tissue being manipulated (e.g., operated on, cut, drilled into, etc.). The above are non-limiting examples of tools that can be utilized with the current disclosure, and one skilled in the art will appreciate that several other now or hereafter known tools may be utilized. An optional tool receiver plate (not shown) can be designed with a quick connect or other feature for easy coupling or decoupling of tools to the robotic arm 111 (e.g., directly and/or via the force sensor 127 when the receiver plate is included in or attached to the force sensor 127), by the operator, while allowing a sterile barrier (such as with a sterile drape) between the tool 129 and the rest of the local sub-system 1100. In certain embodiments, the tool receiver plate can be a component (master side) of an automated tool changer such as the QC-001 tool changer from ATI Industrial Automation NC. In such automated operation, it is envisioned that the robotic arm 111 may move automatically to a tool tray (not shown), place an existing tool in the appropriate slot, pick up the new tool, and return to a stand-by position ready for the next step. The robot wrist 114 or receiver plate on the force sensor 127 may be designed with the appropriate mating features to interface with the tool 129 including provision for power and communication lines.

A calibration step may, optionally, be performed to determine a positional relationship between the tool tip and other components of the local sub-system 1100 (e.g., the robotic arm 111, the robot base, etc.) in order to determine an accurate forward kinematics information across the entire chain of serial linkages within the local sub-system 1100 (e.g., from base to tool tip). Such calibration may be entirely or partially performed prior to use or as part of periodic maintenance using any now or hereafter know calibration methods.

The local sub-system 1100 may also include a computing device 115 configured to receive information (from, for example, the camera 126, the referencing means, the force sensor 127, the remote sub-system 1500, a user via input devices, etc.), analyze the received information, and provide instructions to control movement and/or operation of the robotic arm 111, tool(s) 129, base 116, the referencing means (e.g., arm 131), vision system with at least one camera 126, the force torque sensor 127, and/or other components of the local sub-system 1100. The computing device 115 may store computer program instructions, for example, within a non-transitory computer-readable storage medium such as a persistent magnetic storage drive, solid state drive, etc. The execution of those instructions may control the entire local sub-system 1100 or components thereof. For example, when executed by a processor of the computing device 115, the instructions may cause the components of the robotics system to actuate the robotics arms, and control the surgical tools. For example, in response to receiving a control signal, the motors in the joints/linkages of the robotics arms may position the arms into a certain posture or position. Optionally, the computing device 115 may be in communication with the remote sub-system 1500 (e.g., a computing device therein). In some embodiments, the computing device 115 may be included in the base 116.

In certain embodiments, robotic arm 111 and computing device 115 may be purchased as an off-the-shelf robotic sub-system or be custom designed using off-the-shelf modular robotic joints and custom linkages. An example of an off-the-shelf robotic sub-system suitable for us in the disclosed invention is the UR5 collaborative robot by Universal Robots, Denmark or the i5collaborative robot by Aubo Robotics, USA. Example of modular robotic joints suitable for use in a custom designed sub-system in the disclosed invention are the Aubo Robotics modular robotic joints (MRJ).

The local sub-system 1100 may also include a user interface and a display screen. Examples of such user interfaces may include, for example, a touch screen, a keyboard, an audio interface (speaker/microphone), a user input device for hands-free operation and/or control of robotic arm 111, or the like. For example sub-system 1100 may include one or more foot pedals 124 communicatively coupled to computing device 115. The foot pedal may include a switching or triggering functionality and/or provide an output proportional to the pedal position. For example, foot pedal 124 may allow the user to switch between hand-guided, semi-autonomous, and/or autonomous modes of operation of the local sub-system 1100. Alternatively, the foot pedal may allow the user to control the speed of robot motion and/or turn on and off the surgical tool. In lieu of or in addition to the foot pedal 124 sub-system 1100 may also comprise one or more joysticks 125 communicatively coupled to computing device 115. One or more of the joysticks may optionally be a haptic device designed to not only provide functionality similar to those from foot pedal 124 as described above but also provide haptic or tactile feedback. Example haptic devices suitable for use with the disclosed invention are the Phantom Premium and Touch devices from 3D Systems, SC. Alternatively, the joystick 125 may incorporate an actuator-based haptic device. Such devices give the illusion of touch, texture, and forces by stimulating the skin in specific patterns. An example of such a device suitable for use in joystick 125 is the 3D Haptics product from Miraisens, Japan. Joysticks 125 may be placed on or attached to the operating table, on a separate pedestal/cart, be hand-held or be integrated on wrist 114 of robotic arm 111.

As used herein, a hand-guided operation refers to a mode of operation when the computing device 115 is configured to allow the robotic arm 111 to support itself against gravity and be compliant in all directions to user imparted force such that a user may hold the robotic arm and/or the tool attached to the robotic arm, and move the robotic arm/tool around freely in any direction (optionally, no-go zones may be employed on the hand-guided movement for safety, integrity of the robotic system, and/or other reasons, that prevent the user from encroaching such no-go zones). In a semi-autonomous mode, the user may control the robot's motion directly through one or more controllers (e.g., joysticks, foot pedal, etc.) or by imparting forces on the tool attached to the robotic arm similar to the hand-guidance mode as described above. In such a mode the computing device 115 may impose real-time constraints on the movement of the robotic arm 111 such that is complies with a planned trajectory or task plan. For example, the user input may, without limitation, provide a motion command such as "forward/backward", "go/no-go" etc. while the computing device 115 may constrain the motion to be consistent with the planned trajectory or task. In an autonomous mode, the user may provide commands to the to the computing device 115 and the device may use the commands in combination with the task plan, planned trajectory, sensor information, control parameters etc. to send appropriate commands in real-time (or near real-time) to control the robotic arm 111 and any surgical tool(s) attached to it autonomously without further user input. However, in such an autonomous mode of operation, a user may still have the ability to stop or override the action robot motion and/or operation via a dead-man switch or foot pedal 124 for reasons such as safety of the patient, failure of one or more components, etc.

Sub-system 1100 may also include one or more means to reference the patient. Such referencing ensures positioning of the robotic arm 111 and/or tool 129 relative to the patient's anatomy at a desired accuracy. The referencing can be rigid or dynamic. In rigid referencing a fixed positional relationship between the robot and the patient is ensured via, for example, a rigid arm 131 having one end fixed at an anchor point on or around the robot base (and/or other components of the local sub-system 1100) and the other end fixed or anchored at a point on the patient's anatomy. The end anchored on the patient's anatomy is preferably rigidly attached to the patient's bony anatomy. In the case of spinal surgery shown as a non-limiting example in FIG. 1, rigid arm 131 can be attached to a vertebra of the patient. It can also be attached to the pelvis or any other rigid anatomical feature. The attachment can be achieved using pins, clamps, and or screws commonly used in orthopedics. For other surgeries like knees, hips, ankle, etc. other bones of interest can be similarly referenced. For example, the rigid arm 131 may be attached to the femur or tibia for knee surgery. The end of the rigid arm 131 anchored to the robot base can be rigidly attached using conventional mechanical attachments like screws, bolts, and clamps. The rigid arm 131 may have one or more links, joints, etc. configured to provide one or more degrees of freedom to the rigid arm 131 for ease of attachment to both the base and patient. However, upon suitable anchoring of the ends, a means to lock down the degrees of freedom can be provided such as, without limitations, mechanical components including with screws, bolts, and clamps. In lieu of or in addition to the rigid arm 131 that directly attaches to the robot base and the patient anatomy, indirect rigid referencing of the patient can be achieved via, for example, two rigid arms—one that is attached from the robot base to the patient table (e.g., using clamps) and the other that is attached from the patient table to the patient's anatomy. These arms together form a chain of rigid coupling from robot base to operating table and from operating table to patient and achieve the same objective as a single rigid arm. Other rigid referencing means such as a ring that encircles a patient's anatomy (e.g., around the skull, chest) are also within the scope of this disclosure.

In some scenarios, it may be desirable to dynamically reference the patient such as, for example, during knee or ankle surgery when significant movement of the bone during surgery can be expected. As opposed to rigid referencing that relies on locking down the positional relationship between the patient and the robot base (or other components of the local sub-system 1110), dynamic referencing tracks positional changes of the patient relative to the robot base or other components of the local sub-system 1110), and utilizes the tracked changes to appropriately adjust the tool position and/or planned trajectories to account for the change in patient position (for example, if a patient moves by "x" distance to the left; the tool position and/or the planned trajectories may be similar adjusted). Such dynamic referencing can be achieved by using an arm 131 that has one or more degrees of freedom as described previously but is additionally equipped with encoders communicatively coupled to one or more computing devices to track the position of moving anatomy relative to the robot base. The arm may be anchored to the robot base at one end and the patient's bony anatomy such as a vertebra on the other end similar to rigid referencing. An example arm suitable for dynamic referencing is the MotionArm600-EP from Refined Motion Engineering, CA.

Alternatively and/or in addition, to the above method of dynamic referencing, the optional vision system comprising camera 126 as previously described can be used for dynamic referencing. In such examples, the vision system tracks anatomical surface information in real-time or near real-time and repeats registration (as will be described later) when significant movement is detected. Alternatively and/or in addition, dynamic reference fiducial(s) (not shown) may be attached to the patient's anatomy and the robot base without the need for a rigid arm connecting arm. The vision system via camera 126 then tracks the positional relationship between the reference fiducials in real-time or near real-time.

Refer now to remote sub-system 1500 as shown in FIG. 1. The remote sub-system 1500 may include one or computing devices 151. The computing device 151 can be one or more of any general purpose or special purpose computing device, server, or some combination thereof consisting of one or more processors, memory (RAM and/or ROM) units, storage devices, power supplies, and other peripherals commonly available for such devices. A server may be any kind of servers or a cluster of servers, such as, without limitation, Web or cloud servers, application servers, backend servers, or a combination thereof. The computing device 151 may store and/or access computer program instructions, for example, within a non-transitory computer-readable storage medium such as a persistent magnetic storage drive, solid state drive, etc. The computing device 151 may be communicatively coupled with the computing device 115 of the local sub-system 1100, the vision system comprising one or more cameras 126, and/or force sensor 127 and the execution of those instructions may control the entire local sub-system 1100 or components thereof. The computing device 151 may receive data from the local sub-system 1100 before, during and/or after performance of a surgical task (e.g., user input data, calibration data, image and/or vision system data, force data, trajectory data, referencing data, diagnostics data, task status, or the like). The computing device 151 may also transfer data to the local sub-system 1100 such as user input data, software updates, tool trajectory plans, registration data, surgical task plans, patient information (e.g., anatomical information), machine learning models and other information.

The computing device 151 may, optionally, be communicatively coupled to and/or display 152 which could also be a touch screen. The computing device 151 may be configured to receive, process, and/or display data on display device 152 (e.g., patient data such as charts, imaging data, surgical task plan, tool trajectory, registration information, or the like) and receive user input via the touch screen or other input devices. Patient data can be accessed from data store(s) such as hospital Picture Archiving and Communications System (PACS) systems, or storage medium, or some other capture device.

The computing device 151 may further be configured to autonomously perform and/or allow a user to perform surgical task planning, tool trajectory planning, and/or virtual surgery (e.g., on patient image data which may include 3D modeling of the anatomy including any hardware to be placed in the anatomy). The virtual surgery may include simulations that show modifications to the anatomy as the surgery is executed. Example surgical planning software that can be used with the disclosed invention is the MediCAD software by Hetec, Germany. In certain embodiments the display device 152 may be a virtual reality headset and associated hand-held controllers via which the user may perform virtual planning and surgical simulations either alone or in collaboration with other users. An example virtual reality headset suitable for use with the invention as disclosed is the Oculus Rift VR headset from Facebook, USA.

As previously mentioned, the computing devices 151 of sub-system 1500 and 115 of 1100 may be communicatively coupled whether remote from each other or in close proximity and when communicatively coupled they may share computing responsibilities and in certain embodiments may also share cloud computing resources. In one embodiment when performing certain operations as disclosed herein, the remote sub-system 1500 may be configured to be in the same room as the local sub-system 1100. In this case, the user of the remote sub-system and the local sub-system could be the same person or the surgeon could be the user of the remote sub-system and his/her assistant could be the user of the local sub-system. In this latter embodiment, the computing device 151 of the remote sub-system may be communicatively coupled to the computing device 115 and/or other components of local sub-system 1100 via a wired connection using common communication protocols such as ethernet, etherCAT, RS-485 etc or a wireless connection using Bluetooth, WiFi or other such wireless protocol. In other embodiments the remote sub-system 1500 may be in a different location than sub-system 1100 and communicate via network 1101 as previously described. The communication link may be used to transfer information needed for task execution such as planning and patient imaging/modeling data, registration data, calibration data, vision data, trajectory data, force data between the remote and local sub-systems and optionally command-control signals from the remote sub-system for supervision and control of the surgical procedure. The local subsystem may communicate back status of the task execution, user inputs, simulations of planned robot motions, force data, and images from vision system camera 126 back to the remote sub-system.

In some embodiments, the remote sub-system 1500 may include elements of a telehealth system wherein computing device 151 is communicatively coupled to a video camera, speaker, and microphone to facilitate video conferencing between a remote operator and a local operator. In such an embodiment, the remote sub-system 1500 may be placed in location remote from the local sub-system so that such capabilities are useful for communication between the operators of the remote and local sub-systems. For example, the remote sub-system can be in large room and may communicate with multiple local sub-systems or the remote sub-system can be in a different room or in a completely different location.

In certain implementations, the remote sub-system 1500 may be configured to share supervisory and/or control responsibilities with the local sub-system 1100. For example, remote sub-system 1500 may be communicatively coupled to a joystick and foot pedal, much like joystick 125 and foot pedal 124 of the local sub-system, allowing a remote user to control and/or supervise and/or control the robot (i.e., local sub-system 1100) in the execution of a task, optionally, with assistance from a local operator of the local sub-system 1100. This will allow a skilled surgeon from afar to perform complex robotic surgeries with assistance from lower skilled local operators. For safety reasons, the local operator may have the ability to override or discontinue remote control operation of the robot at any time.

In another embodiment, the robotic subsystems 1100 and 1500 may be iOT (Internet of things) devices connected to a wide area network (WAN) and the internet with the local sub-system 1100 accessible by multiple authorized remote subsystems 1500 and multiple remote operators or a single authorized remote sub-system 1500 able to access multiple local sub-systems 1100.

Sub-system 1500 may also be communicatively coupled one or more optional "local" display devices 120 placed close to the surgical field. The display device could be a touch screen serving as both a user interface to take commands/inputs from the user as well as display information to him/her. The information displayed may include, for example, the surgical plan, the execution status of such plan, simulations of planned execution, error/alarm messages, or any such relevant information in 2D or 3D. In one embodiment the local display device is an augmented reality or mixed reality headset 121 worn by the user and capable of displaying virtual information overlaid on the real-world as seen by the user such as an overlay of the surgical plan and tool position in relation to the plan on the patients anatomy. Example of such an augmented or mixed reality headset is the Microsoft Hololens by Microsoft, Inc WA. The headset may also be equipped with a microphone communicatively coupled to computing device 151 wherein the computing device is configured to receive audio inputs and commands from the user. It may also be equipped with a speaker communicatively coupled to computing device 151 to provide audio feedback to the user.

Figure 2:
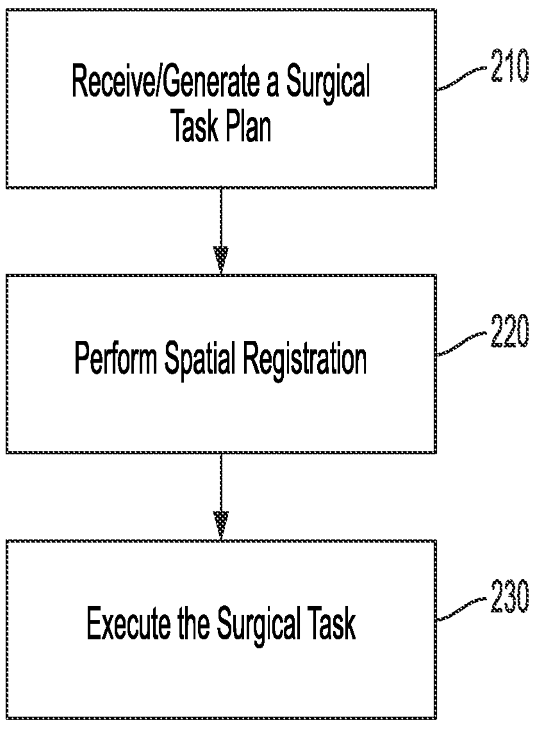
FIG. 2 provides a flow chart illustrating an example method of performing surgical tasks involving modification or manipulation of hard tissue using the collaborative robotic system of this disclosure.

Refer now to flowchart 200 FIG. 2 that illustrates an example method for performing a surgical task autonomously or semi-autonomously using the robotic system of FIG. 1. The method involves a planning step 210 for generating and/or receiving a surgical task plan to be executed by the robot. The surgical task plan may include, for example, a location of at least one entry point that a surgical tool may use for accessing or entering a tissue to be manipulated. The task plan may also include a trajectory of a working surface/end of the surgical tool (e.g., a tool tip) inside the tissue. The surgical task plan may be provided by a user (for e.g., a surgeon) and/or be automatically generated based on patient anatomical information, surgical task goal, previous similar trajectories, etc. For example, in a procedure performed on the spine of a patient, the method may include identifying various entry points, target points (e.g., in/on a particular vertebra), and trajectories between the entry and target points using any now or hereafter known methods. Trajectories can include any path that interconnects the target points and the entry points. For example, if one target point and one entry point is determined, a trajectory can include a straight line or curved line connecting the one target point and the one entry point. The trajectories can be based upon various information, such as the instrument that will move along the trajectory, the guiding system, and other appropriate information or limitations. For example, if a rigid instrument is to be used in the determined procedure, for example an instrument that is unable to curve, then only straight trajectories will be determined from the entry point to the target point. The system can further determine a cost function for each of the selected trajectories, entry points, and target points based on various rule sets (e.g., chose the shortest feasible trajectory, avoid blood vessels, nerves, etc.), historical data relating to similar procedures, patients, etc., user input, or the like. It will be understood by one skilled in the art that other feature or procedure portions can also be determined and associated costs associated therewith by the planning system, such as length of path, time of procedure, etc.

Target points can include any appropriate anatomical target points, such as the position of a hard tissue to be manipulated, the position of an intended implant, position of a tumor or growth, position of the region to be removed, or the like. The anatomical target points can be determined based upon the data acquired of the patient and other appropriate data. The anatomical target point can include one or more points as defined by the anatomy and can be represented as image or virtual target points in the data acquired of the patient. For example, the virtual target points can include one or more voxels in three dimensional image data or portions of a voxel from three dimensional image data. It will be understood, that an anatomical target point can be determined based on image or other data and the anatomical target point can then be represented on a display device relative to the image data as a virtual target point. A determination of an entry point can be made to reach the determined target points and may include, for example, incision areas, burr hole creation areas, cutting planes, and other appropriate entry points. The determination of the entry points can be based upon any appropriate data, such as the determined anatomical target points, or patient data. The entry point or entry points selected for analysis can include a limited number of points or all possible points. Similar to target points, the entry points can be anatomical entry points which can then be illustrated as virtual image points. As such, the planning step 210 may be performed relative to patient image data such as from a CT or MRI scan (e.g., on remote sub-system 1500). In certain embodiments, to facilitate planning a 3D model of the patient anatomy may be derived from the patient image data or a database of generic or patient-specific models that can optionally be "virtually deformed" to better match the patient's specific profile or patient's 3D or 2D image data. The planning, performed in an image coordinate frame, may comprise plan(s) for common musculoskeletal procedures like drilling, burring, screwing, plating, cutting, osteotomy etc. The planning may, optionally, include simulations of the surgery including post-operative simulations showing the modified tissue and result of the surgery.

The method may further include a registration step 220 to acquire a spatial relationship between the image coordinate frame in which the planning was performed and the robot coordinate frame in which the task will be executed. The robot coordinate frame is typically the world coordinate frame in which the patient and the robot are positioned (for example, on vertebra 134 as patient lies on the table in the operating room). The image coordinate system describes how an image was acquired with respect to the anatomy of the patient. An example image coordinate frame may be a patient coordinate frame such as the RAS (Right, Anterior, Superior) coordinate frame and the registration step in this case may involve determination of the spatial transformation from RAS frame to the robot frame.

Figure 3:
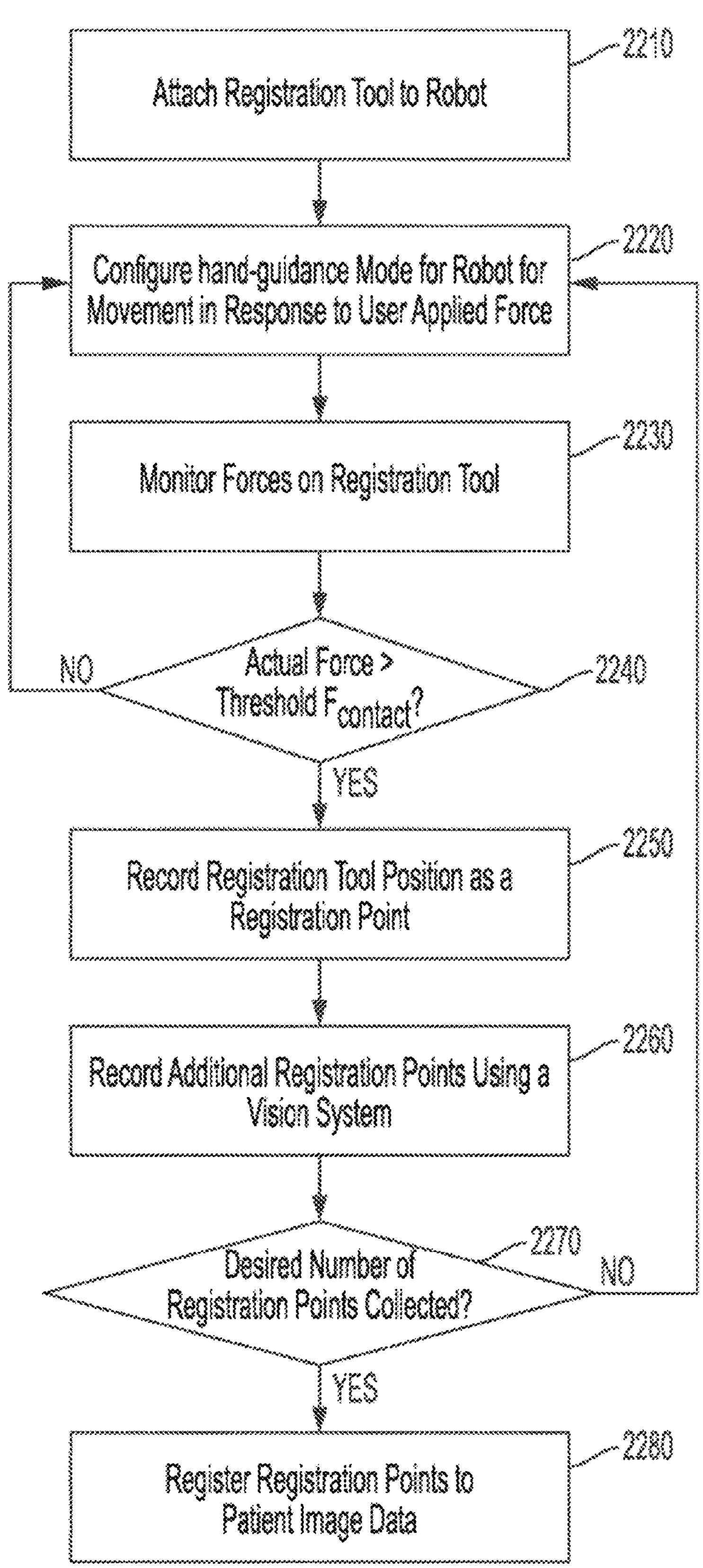
FIG. 3 provides a flow chart illustrating an example registration step as disclosed herein.

A flowchart illustrating an example registration method for determining the above spatial relationship between the image coordinate frame and the robot coordinate frame is shown in FIG. 3. At step 2210, the method may include attachment or coupling of a registration tool to a robotic arm (e.g., at the wrist of the arm). The registration tool may be attached to the robotic arm while the robot is in a standby position (i.e., not actively engaged in executing a surgical task). The registration tool can be any generic elongate tool of suitable length that allows point contact with the anatomy and/or tissue of a patient while the patient is in the same position as that of a surgical task execution. The registration tool may be an off-the-shelf probe tools commonly used in coordinate measurement machine (CMM) systems. An example probe that can be used for the registration method described herein is Renishaw RMP60 compact spindle probe with or without a swivel from Renishaw, United Kingdom. The registration tool may also be the surgical tool that will also be utilized for tissue modification in the execution and/or planning step as will be described later.

A calibration step may be performed to accurately determine the tip (or working end) position of the registration tool in the robot coordinate frame. Several methods to perform such calibration exist in the art. For example, calibration may be performed using a pivot calibration method that consists of rotating the tip around a stationary point to determine the tip's 3D position in the robot coordinate frame. Once the registration tool is attached and calibrated to the robotic arm, a reference force value $F_{reference}$as measured by the force sensor may be determined. For example, determining the reference force value $F_{reference}$ may include measuring an average force (e.g., average gravitational forces) acting on the force sensor in the standby position. The $F_{reference}$ may be used to zero out the effect of gravity and other forces from the measured force such that the true contact/interaction force is measured when the registration tool is in contact with the anatomy.

At 2220, the robot may be configured to be in a hand-guidance mode that allows the user to move the registration tool tip towards a first registration landmark or surface on the patient's tissue and make contact with it. In such hand-guidance mode of operation, as previously described, the robotic arm moves in the direction of forces imparted by a user.

When the user makes contact with the tissue, the system may monitor the changes in forces measured by force sensor relative to the above reference force to determine an actual force applicable on the tip (where, $F_{actual}=F_{measure}-F_{reference}$) (2230). The system may then determine whether the actual force ($F_{actual}$) is greater than or equal to a threshold $F_{contact}$, $F_{contact}$ being indicative of a position of the tip that is in contact with the tissue at a first pre-selected landmark or surface (2240). Upon determining that $F_{actual}$ is greater than or equal to $F_{contact}$, the system may record the tip position as a registration point (2250). The system may, optionally, stop movement of the tool tip at the registration point. If the $F_{actual}$ is less than $F_{contact}$, the user may continue moving the registration tool in the hand-guidance mode until sufficient contact with $F_{actual}$ greater than $F_{contact}$ is made.

Alternatively and/or additionally, information received from a vision system (comprising one or more cameras or other imaging devices), a LIDAR sensor, or another sensor system as previously described) may be utilized to further collect additional surface registration points in a region of interest close to the registration point (2260). In such an embodiment, the vision system may be calibrated such that the relationship between the vision system's coordinate frame and the robot coordinate frame is known, using any now or hereafter known calibration techniques, such as the hand-eye calibration technique. In addition, the region of interest may be pre-defined as a 3D bounding box relative to the tool tip and have a size/volume based on the anatomy of interest and/or number of surface registration points to be collected (for example, the bounding box may be a cuboidal box (or any other 2D/3D shape) around the registration point whose size is determined based on anatomy of interest and/or number of surface registration points to be collected). Typically, when vision systems are used, segmentation of the surface information captured by the vision system to extract out the region of interest from the field of view of the camera (which could be a large area encompassing the entire surgical field) poses a significant problem. The definition of a region of interest relative to the tool tip (as described above) solves this problem, and provides a novel means to segment the surface information. Only the surface that falls within the 3D bounding box relative to the tool tip is segmented out from the data set and utilized to determine the surface registration points. For example, when the surface information is represented as a point cloud, the portion of the point cloud that falls within the bounding box may be collected as additional surface registration points. Once registration is complete, the region of interest may be fixed relative to the surface registration point(s) collected and continuously monitored and tracked by the vision system as a means of dynamic referencing.

At 2270, the system may determine whether a desired number of registration points (e.g., a number of registration points that covers the anatomy of interest) has been collected. If not (2270: NO), the system may repeat steps 2220 to 2260 to collect additional registration points that are typically spatially well distributed to cover the anatomy of interest by allowing the user to continuously move the tip over the region of interest. The user guided registration tool tip motion may, in certain embodiments, be a trace motion where the tip stays in contact with the tissue or it can be an intermittent contact motion (probing), or some combination thereof In either case, surface points may only be recorded as registration points when the $F_{actual}$ is greater than or equal to $F_{contact}$ and the registration point is positionally distinct from a previously recorded registration point by a minimum value. The total number of registration points may range from tens to thousands and may in some cases include millions of points depending on the application, the particular embodiment as described herein, and the resolution of the vision system (if applicable). After an adequate number of registration points are collected, the dataset including the registration points may be processed to, for example, remove noise, outliers, etc. using algorithms well known in the art. The dataset may, optionally, be processed to create a registration surface.

If a desired number of registration points has been collected (2270: YES), at 2280, the system may register the registration points and/or surfaces to landmarks and/or surfaces on the patient image data (i.e., determine a spatial relationship or mapping between the registration points and points on the patient image data). Such spatial relationship may be represented as a transformation matrix or any other mathematical representation of spatial transformation well known in the art.

Several algorithms in the art exist to perform such registration (e.g., rigid transformation and/or non-rigid transformation). For example, a registration algorithm may include a coarse registration to roughly map the registration points to the patient's image followed by a fine registration. For example, coarse registration may be performed manually by a user by positioning and orienting the camera of the vision system and registration tool tip when in contact with the anatomy such that the real-time image of the tissue as captured by the camera and displayed on the display device is roughly aligned to a reference image of the contacted anatomy (e.g., created from previously collected image data) that is also displayed. The real-time and reference images can be displayed side-by-side or as an overlay. Additionally and/or alternatively a fine registration algorithm may be utilized including, for example, Iterative Closest Point (ICP) algorithm and/or the like. The input to the fine registration algorithm are the registration points collected (with or without coarse alignment), and the locations of the corresponding landmarks and/or surfaces in the image. With these two inputs, the algorithm calculates the spatial relationship between the anatomic and robot coordinate frames using an iterative process that minimizes an error metric.

After registration, an accuracy verification may, optionally, be performed by placing the tool tip on a tissue landmark (e.g. spinous process of vertebra 134) and displaying on the display device a virtual image of the tool in relation to the tissue in the image data and a real-time image of the same tool and tissue as captured by the vision system. This provides a visual means to the user to verify the accuracy of registration. The registration may be repeated on-demand or repeated automatically in real-time or near real-time, if movement of the anatomy in the region of interest is detected by the vision system.

Once this spatial relationship, typically encapsulated in transformation matrix(ces) well-known in the art, is acquired, the task plan information may be converted/mapped from the image coordinate frame to the robot coordinate frame in order to provide the robot with the necessary real-world trajectory to execute. Accurate determination of the above spatial relationship is, therefore, vital to precise execution of the surgical task.

Figure 4:
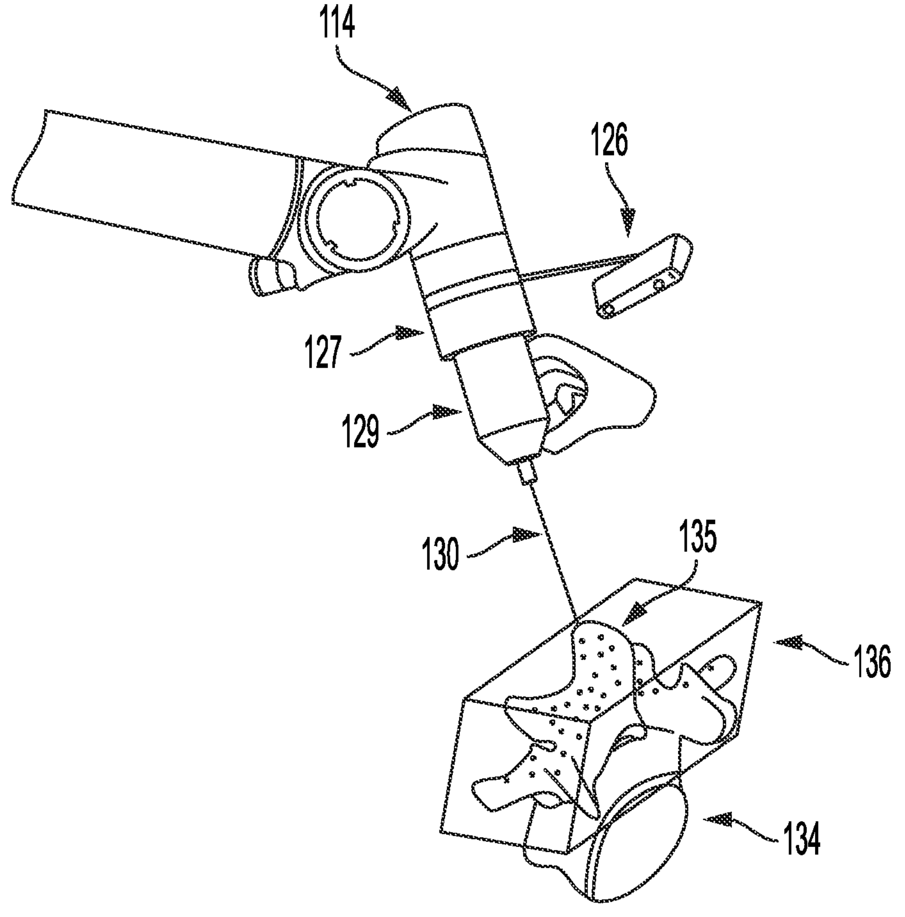
FIG. 4 is a schematic diagram illustrating a collaborative robotic system of this disclosure executing an example registration step.

Refer now to FIG. 4 for a graphical representation of a portion of the local sub-system 1000 of FIG. 1 engaged in the registration step (described with respect to FIG. 3) for registering a patient vertebra 134 to its image data. As shown in FIG. 4, the registration tool 129 with an elongate tool bit 130 is moved to contact, via user action (i.e., in hand-guidance mode of operation), landmark (spinous process) 135 on vertebra 134. Every time, the determined force on the tool tip is greater than or equal to the threshold force, the corresponding contact point position is recorded as a registration point. The process may be repeated until a desired number of registration points is collected, and are registered to the landmark (i.e., the spinous process in the non-limiting example in FIG. 4). Optionally, at the same time or soon after, additional points in a region of interest 136 may be collected using the vision system via camera 126. The region of interest in this example is defined as a 3D bounding box of suitable size to cover surfaces surrounding the spinous process 135. Once the registration points are collected and registered to a patient's image data, they can be monitored in real-time by the vision system during task execution in real-time or near real-time and the registration may be repeated when a significant change is detected, thereby dynamically referencing the anatomy. Numerous other 3D to 3D and 2D to 3D registration algorithms exist in the art and may also be utilized with the disclosure in addition to and/or as an alternative to the above registration process. For example, a common algorithm well known in the art is image-based registration relying on collecting one or more patients image or images with a distinct marker or fiducial in the field of view, such as one placed on vertebra 134 or a nearby vertebra or pelvis or attached to robot wrist 114, whose positional relationship relative to the robot base and patient is fixed and/or known. From the above image or images the position of the fiducial or marker in the image coordinate frame is also determined using algorithms well-known in the art. From these two pieces of information the spatial relationship between the robot and image coordinate frames can be calculated. One skilled in the art will appreciate that the robotic platform disclosed is agnostic to the method utilized to determine the above spatial relationship.

Referring back to FIG. 2, the method may further include execution of a surgical task (e.g., tissue modification) by the robot, autonomously or semi-autonomously under human supervision and/or control (step 230), based on the task plan in the robot frame of reference. Prior to such execution, an appropriate surgical tool suited to the planned surgical task is attached to the robotic arm manually and/or autonomously. For example, a drill may be attached to the robotic arm for a surgical task that involves drilling. The tool is calibrated such that the tool tip position in the robot frame is known. As previously described, a pivot calibration step may be utilized. A quick connect/disconnect mechanism may be utilized to make the attachment operation easier for the user. Alternatively, the process could be automated so that the robot autonomously moves to a tool holding tray and picks up the appropriate tool. The tool may incorporate a identification chip or marker for identification/verification by the robot and/or have a preset storage location on the tray.

Figure 5:
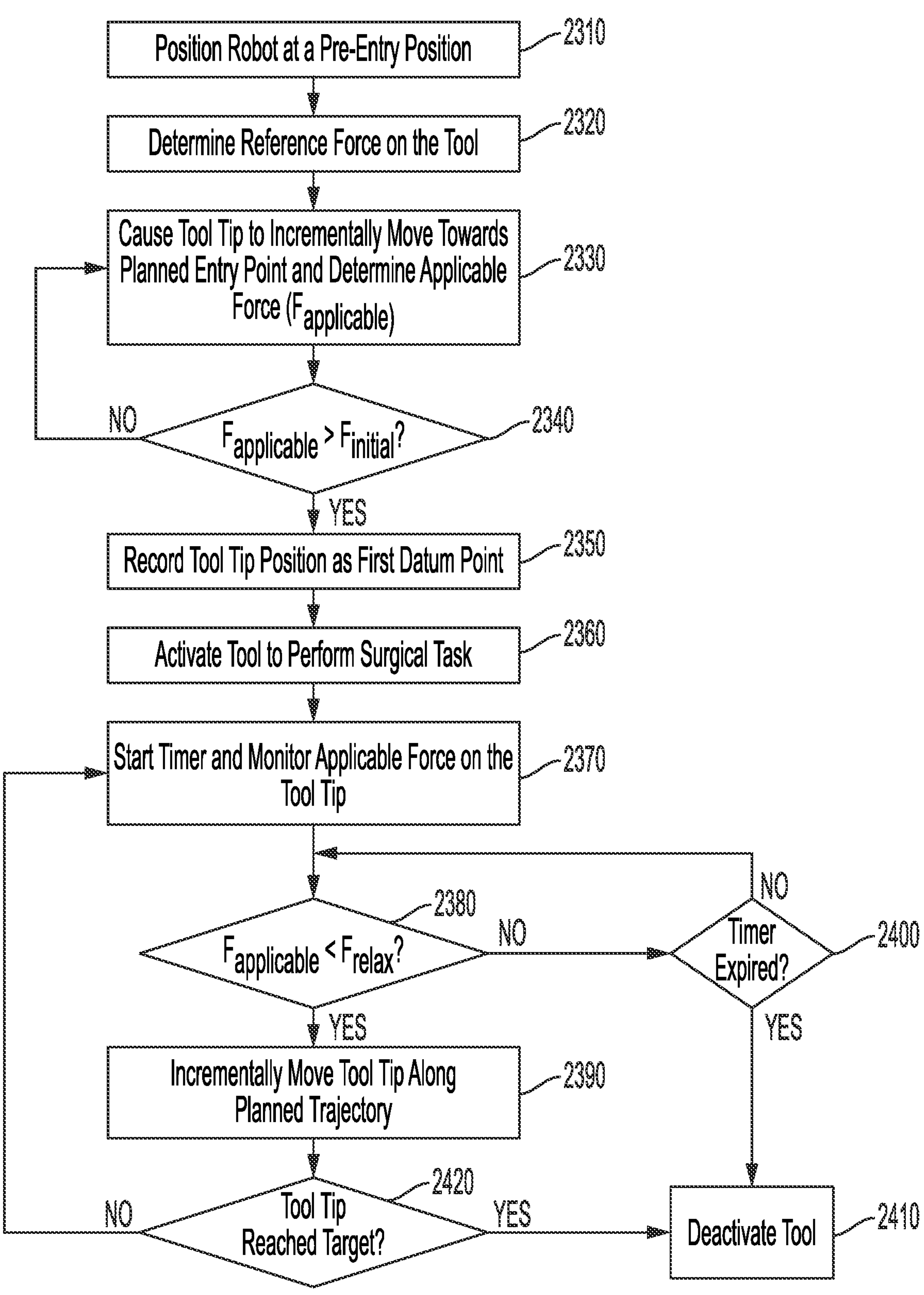
FIG. 5 provides a flow chart illustrating an example method of controlling a surgical tool attached to a robotic arm of the example collaborative system for executing a tissue modification task.

FIG. 5 provides a flow chart illustrating an example method for executing the surgical task by the robot. The system may receive a task plan including a tool trajectory, entry point, and/or target point (as discussed above). As shown in FIG. 5, 230 comprises a step 2310 that causes the robot to move from a stand-by position (any arbitrary position when the robot is not performing a surgical task) to a pre-entry position in which the tool tip (or another working end) is positioned in proximity (e.g., within a threshold distance) of the planned entry point. Optionally, positioning the tool tip at the pre-entry position may also include orienting the tool at (or within a threshold) desired angle of entry.

The system may determine the pre-entry position autonomously based on, for example, the task plan information (including the entry point position and desired tool tip angle at entry), tool type, current position, or the like. For example, the pre-entry position may be a point in space over the planned entry position that is less than 2 cm from the planned entry position, and approximately at the desired entry angle. Alternatively and/or additionally, a user may cause the robot and/or the tool tip to move to the desired pre-entry position using, for example, user input using a joystick 125 and/or by a user applying manual force on the tool 129 or wrist 114 with the robot in hand-guidance mode. In the case of autonomous motion, for safety reasons, it is anticipated that the user may still control the robot motion using a foot pedal 124, joystick 125 or by imparting force on the tool 129. For example, the user may be able to control the tool motion in semi-autonomous mode only along the planned trajectory in a forward or reverse direction. The robot motion in this step 2210 may also be a combination of hand-guidance motion and autonomous motion wherein a first hand-guidance motion may coarsely position the tool over the entry point, and the pre-entry position may then be refined autonomously by the robot. Appropriate visual and/or audio cues on a display device can guide such motion.

The method further include determining a reference force on the tool tip while the tool tip is in the pre-entry position (2320). Examples of such reference force may include, without limitation, a gravitational force, inertial force, frictional force, or any other force that does not represent the contact force of the tool tip with the anatomy. The system may determine the reference force by averaging (or otherwise analyzing) the force measurements from a force sensor included in the robotic arm or coupled to the tool (e.g., force sensor 127). For example, the system may determine a reference force including gravitational force by calculating the center of gravity of the tool and the force sensor assembly, and using that in combination with the kinematic information about the position of the robot end effector (i.e., the surgical tool) to determine the gravity force vector. Accounting for the reference force in the planned trajectory increases the accuracy of the executed task and trajectory followed by the tool tip. For example, the system may compensate for the reference force to determine the amount of force to add to or subtract from the force sensor readings during task execution (e.g., to remove/subtract the effect if gravity on the tool tip). The outcome is a more accurate measure of the contact force (e.g., at point of entry or during tissue manipulation), which allows for more accurate execution of the control algorithm.

At 2330, the system causes robot to make autonomous incremental motions (e.g., 1 mm, 2 mm, 3 mm, or the like) of the tool tip towards the planned entry point, and determines the force applicable on the tool tip at each incremental position. The applicable force may, for example, be the force measured by the force sensor relative to the previously collected reference such that $F_{applicable}=F_{measured}-F_{reference}$.

At 2340, the system may compare the value of $F_{applicable}$ (at each incremental position) to that of a threshold force value ($F_{initial}$) representative of an initial contact force of the tool tip with the tissue to determine whether $F_{applicable}$ is greater than or equal to the threshold. The threshold force value can be set arbitrarily at first and refined empirically based on actual data, determined using machine learning algorithms, determined from the stiffness and/or material properties of the tissue being manipulated, and/or the like. If $F_{applicable}$ is greater than or equal to the threshold (2340: YES), the system may record the tool tip position as a first datum point—representing the entry point from which the tool tip trajectory inside the tissue will be measured (2350). If $F_{applicable}$ is less than the threshold (2340: NO), the system may continue performing steps 2330 and 2340 for a predefined number of attempts, distance, and/or time defined by a search limit $ds_{limit}$. The search limit can be set arbitrarily or determined based on the proximity of the pre-entry position to the entry point, the magnitudes of the programmed incremental motions, and/or any safety considerations for the procedure while also minimizing the procedure time. If the datum point is not reached within the search limit $ds_{limit}$, the system may execute a command to abort the surgical task execution and cause the robot to return to a stand-by position.

After datum 'A' representing the entry point is successfully recorded, the system may activate the tool (2360) to execute the surgical task according to the task plan and along the planned trajectory (2360).

At 2370, the system may start a timer and simultaneously begin monitoring the force F applicable on the tool tip relative to the previously collected $F_{reference}$ to determine if the applicable force drops below a threshold $F_{relax}$ (2380). The threshold $F_{relax}$ may be determined based on factors such as mechanical properties of the tissue, removal/modification rate of the tissue (that can be further influence by speed and/or power of the tool used), magnitudes of the incremental motions, or the like.

If the applicable force drops below a threshold $F_{relax}$ (2380: YES), the system may cause the tool tip to incrementally (e.g., about 1–10 mm, or the like depending on the type of surgical procedure and other factors) to a next position move along the planned trajectory while monitoring the tool tip position relative to datum 'A' (2390). If the applicable force is not below a threshold $F_{relax}$ (2380: NO), the system may continue monitoring the force $F_{applicable}$ on the tool tip relative to the previously collected $F_{reference}$ unless the timer has expired (2400). If the timer has expired, the system may deactivate the tool and retract tool tip from tissue safely to return the robot to stand-by position using positional information and/or user hand-guidance. (2410). The timer is an optional safety mechanism to ensure that the robot does not get stuck in a potentially unsafe situation where the tool is active but the force F fails to drop due to an abnormal condition. The systems and methods of this disclosure may not implement or use such a timer without deviating from the principles of this disclosure.

At 2420, the system may determine if the tool tip has reached a target point in the tissue (i.e., end of the trajectory—datum 'B'). If the tool tip has not reached the target point in the tissue (2420: NO), steps 2370-2420 may be repeated. If the tool tip has reached the target point in the tissue (2400: YES), then tool deactivation and return to stand-by is executed as above (2410).

Figure 6:
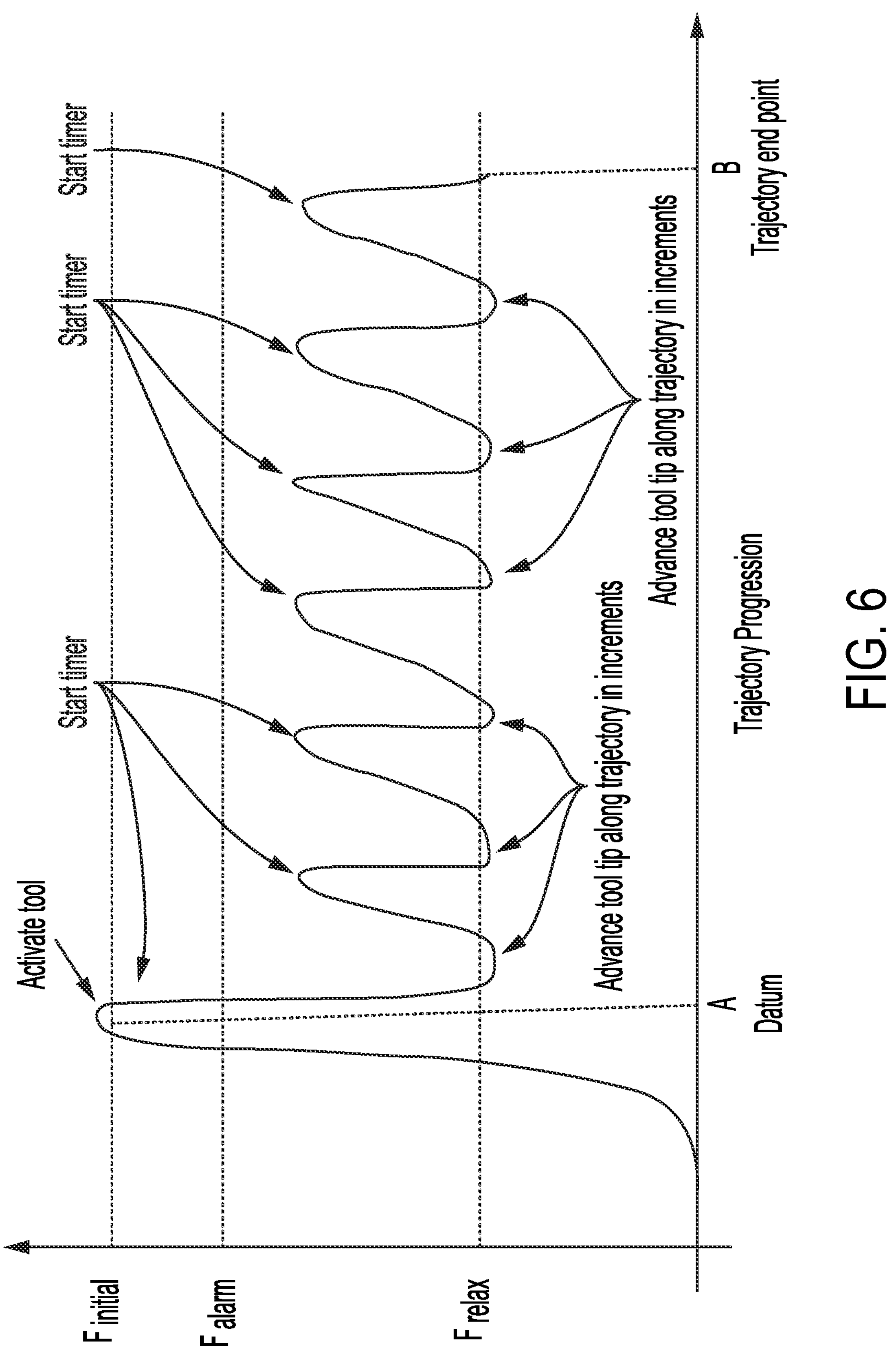
FIG. 6 provides an example graphical relationship between force and tool trajectory profile during autonomous execution of a planned trajectory in a tissue.

FIG. 6 shows an example force F and trajectory profile during execution of the planned trajectory as described above with overlay of specific actions executed by the system (as described above). FIG. 6 is a non-limiting example and one skilled in the art will appreciate that depending on the type of task being executed and the type of tissue being interacted with, the force values, force type (axial forces or torques), directional components of the forces and torques that monitored (Fx, Fy, Fz, Tx, Ty, Tz), the thresholds and related actions can be very different. It is anticipated that specific sequences and threshold values will be developed for different operations. Such sequences and threshold values may be obtained from known properties of the tissue being modified. Alternatively, machine learning techniques may be employed to refine and optimize such values and profiles wherein the training dataset utilized in the machine learning comprises force and trajectory measurements collected during actual or simulated surgeries. In an example of such a machine-learning derived algorithm, the values and profiles may be selected to minimize the difference between the actual and desired forces or to minimize the duration of the task while keeping forces below a threshold.

As shown in the example in FIG. 6, as the tool tip contacts the tissue surface, the applicable force F first rises above a threshold $F_{initial}$ representing initial contact with the tissue, such as cortical bone of vertebra 134. This is recorded as datum 'A' representing the entry point into the tissue. At this point the tool is activated. A timer is also concurrently activated and the force begins to drop as bone is ablated/removed by the tool tip. When the force drops below another threshold $F_{relax}$, the monitored tool tip the tool tip is advanced incrementally along the planned trajectory causing the force to rise again as the bone is engaged by the tool tip. A timer is started again and waits for the force to drop. If the monitored tool position shows that the planned trajectory end point 'B' has not been achieved, the above sequence of steps is repeated until the trajectory end point 'B' is achieved. Optionally an alarm or alert threshold $F_{alarm}$ for the monitored force F can also be implemented for safety. For example, in a drilling operation of a vertebra once the outer cortical wall has been breached and tool tip begins acting on softer cancellous bone, the expected force values are lower that the initial contact force. Therefore the $F_{initial}$ value or some alternate level like $F_{alarm}$ as shown in FIG. 6 can be used as an alarm or threshold to alert the user of an abnormal condition (such as an undesirable contact with outer cortical layer indicative of a breach or imminent breach) or for the system to take action autonomously like stopping the tool action and retracting/returning to the stand-by position.

Figure 7:
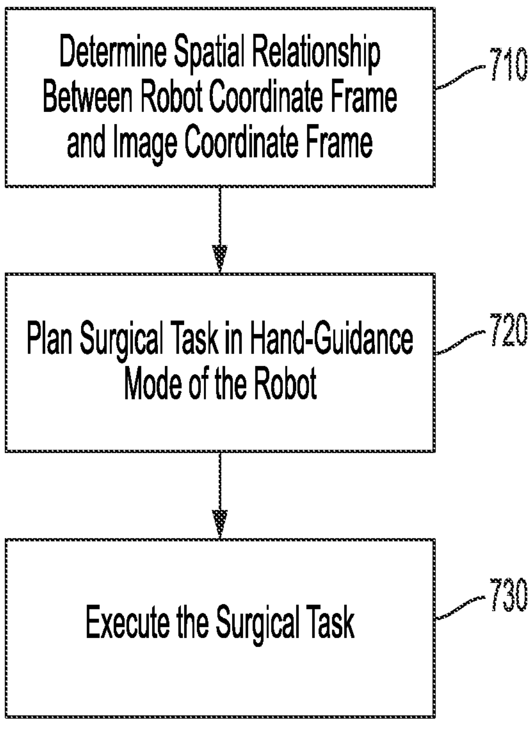
FIG. 7 provides a flow chart illustrating another example method of performing surgical tasks involving modification or manipulation of hard tissue using the collaborative robotic system of this disclosure.

Refer now to FIG. 7 for a flow chart illustrating another example method of performing surgical tasks involving modification of hard tissue using the robotic system of this disclosure. In this embodiment, the spatial relationship between image coordinate frame and robot coordinate frame is determined first using the registration method described above (710). At 720, the system may then plan a tissue modification/manipulation task intraoperatively with the robot in hand-guidance mode (i.e., a user causes the tool tip to move from one position to another). The system may use the robotic sub-system 1100 in communication with sub-system 1500 that has the image data for such task planning. The task plan may include at least one entry point into the tissue and one tool tip trajectory inside the tissue, where the task plan is created by collecting and storing one or more points, via hand-guided tool tip interactions with the actual tissue as the patient is lying on the operating table and the user specifying one or more plan parameters. For example, a user may cause the tool tip to move to a desired entry point in the hand-guidance mode, specify the location of the tool tip as the entry point, and provide one or more plan parameters. At 730, the robot may execute the planned task as described above.

Figures 8A, 8B, 8C:
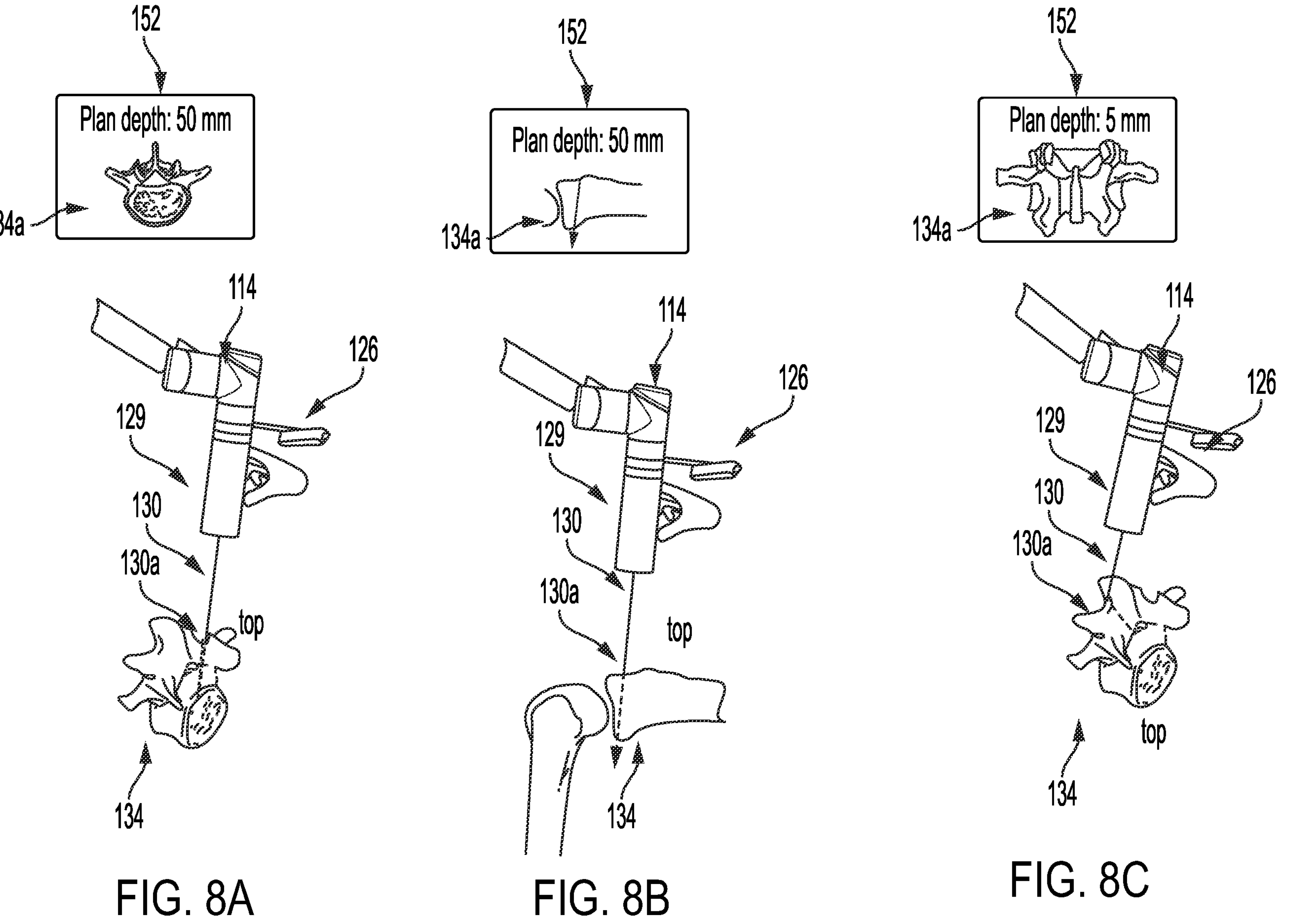
FIGS. 8A-8C are schematic diagrams illustrating the collaborative robotic system performing an example planning method as disclosed herein.

FIGS. 8A-8C are schematic views of example task planning methods performed using the system in FIG. 1 involving user-guided interactions of the tool tip with the tissue and user-specified plan parameters (i.e., step 720). For example in FIG. 8A, the task being planned is drilling into vertebra 134. The tool 129 in this case may be a drill or dremel tool capable of making holes. Typically, such tools may comprise a shaft 130 and tip 130*a*. Given the task of making one or more drill holes, the task plan may contain several plan parameters which in this case may be hole depth, trajectory (angle), and preferably the hole diameter. One or more these plan parameters may be specified by a user. In FIG. 8A, the hole depth parameter is shown as 50 mm and displayed on device 152. The hole locations and trajectories (angle) may be planned by the user by moving the tool 129 (with the robot in hand-guidance mode) and causing the tool tip 130*a* to contact with the surface of the object at the desired locations at the desired angle. These tool positions and trajectories (computed based on the desired depth and angle) may be stored by the system as parameters of the plan. The hole diameter may be planned by selecting the appropriate diameter shaft and/or received as a user input. This method of planning, as described above, eliminates the need for pre-planning prior to the procedure and utilizes human knowledge and perception relative to the actual anatomy to plan the task. In addition to or in lieu of displaying the plan on display device 152 relative to the image data as shown in FIG. 8A, the plan, either during or after planning, may be visualized directly on the patient's anatomy using augmented or mixed reality headset 121 further improving the user's ability to visualize and confirm the plan.

FIG. 8B is a schematic view of another example cutting task planned using the system in FIG. 1 involving user-guided interactions of the tool tip with the tissue and user-specified plan parameters. The tool 129 is this case may be an oscillating saw 130 with a cutting edge 130*a* and the task involves making one or more cuts into knee 134. The task plan may contain at a minimum the cut depth, cut location, cut trajectory (angle), and preferably the cut width. The cut depth may be specified by the user by entering the parameter into the computing devices 151–shown as 50 mm on display device 152 for at least one of the cuts in this example. The cut locations and trajectories (angle) may be planned by the user moving the tool, with the robot in hand-guidance mode, and making the tool edge contact the surface of the object at the desired locations and angles. These tool positions are then stored in the system as parameters of the plan and displayed relative to the image data on display 152.

FIG. 8C is a schematic view of another example scoring (etching) task planned using the system in FIG. 1 involving user-guided interactions of the tool tip with the vertebra 134 and user-specified plan parameters. The tool 129 in this case may be a Dremel-like or burr tool with a shaft 130 and tip 130*a*. Given the task of scoring a path, the plan may comprise at a minimum a trajectory of the desired scoring, a scoring depth, and preferably a width. The scoring depth may be planned by specifying and entering the parameter into the computing device 151—shown as 5 mm for at least a portion of the path. The scoring trajectory may be planned by the user moving the tool, with the robot in hand-guidance mode, and making the tool tip 130*a* contact the surface of the object and tracing the desired path. This path is then stored in the system as a parameter in the plan and displayed relative to the image data on display device 152. The scoring width may be planned by selecting the appropriate diameter shaft 130.

In each of the examples shown in FIG. 8B-8C, just as the example in FIG. 8A, alternatively or in addition the plan, either during or after planning, may be displayed as an overlay on the actual tissue using augmented or mixed reality headset 121.

It is envisioned the above method can be used for even more complex tasks such as burring and/or reaming out of anatomical regions. In such examples, a higher level/more complex plan may be converted into a series of simpler tool tip trajectories as described in the examples above.

Figure 9:
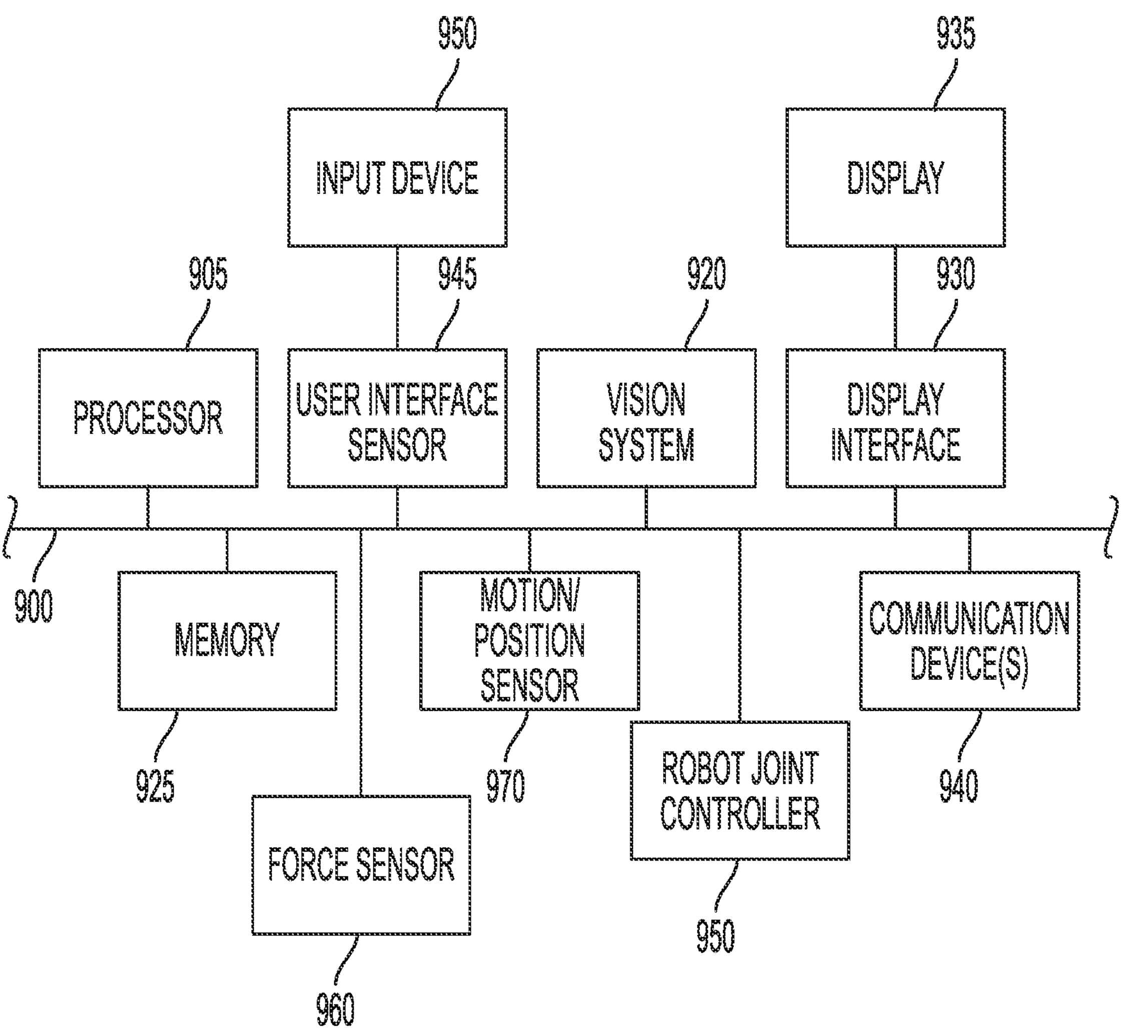
FIG. 9 is a block diagram of elements of a computing device on which the various systems and methods in this document could be implemented.

FIG. 9 depicts an example of internal hardware that may be included in any of the electronic components of the system, such as internal processing systems of the robot, remote sub-system, or the like. An electrical bus 900 serves as an information highway interconnecting the other illustrated components of the hardware. Processor 905 is a central processing device of the system, configured to perform calculations and logic operations required to execute programming instructions. As used in this document and in the claims, the terms "processor" and "processing device" may refer to a single processor or any number of processors in a set of processors that collectively perform a set of operations, such as a central processing unit (CPU), a graphics processing unit (GPU), a remote server, or a combination of these. Read only memory (ROM), random access memory (RAM), flash memory, hard drives and other devices capable of storing electronic data constitute examples of memory devices 925. A memory device may include a single device or a collection of devices across which data and/or instructions are stored. Various embodiments of the invention may include a computer-readable medium containing programming instructions that are configured to cause one or more processors, and/or devices to perform the functions described in the context of the previous figures.

An optional display interface 930 may permit information from the bus 900 to be displayed on a display device 935 in visual, graphic or alphanumeric format, such on an in-dashboard display system of the robot. An audio interface and audio output (such as a speaker) also may be provided. Communication with external devices may occur using various communication devices 940 such as a wireless antenna, a radio frequency identification (RFID) tag and/or short-range or near-field communication transceiver, each of which may optionally communicatively connect with other components of the device via one or more communication system. The communication device(s) 940 may be configured to be communicatively connected to a communications network, such as the Internet, a local area network or a cellular telephone data network.

The hardware may also include a user interface sensor 945 that allows for receipt of data from input devices 950 such as a keyboard or keypad, a joystick, a touchscreen, a touch pad, a remote control, a pointing device and/or microphone. Digital image frames and/or surface information also may be received from a vision system (e.g., a camera) 920 that can capture video and/or still images. The system also may receive data from a motion and/or position sensor 990 such as an accelerometer, gyroscope or inertial measurement unit.

The hardware may also include a dedicated robot joint controller 950 with the necessary control algorithms for position control of the robot including servo-control using encoders and redundancy in computing resources and other safety mechanisms compliant with applicable safety standards. The system may also receive data from a force sensor 960 as previously described.

What is disclosed is a surgical robotic platform designed to share the surgical workspace with humans and capable of completing at least a portion of one or more of surgical tasks involving modification of hard tissue autonomously under human supervision and/or control.

The above-disclosed features and functions, as well as alternatives, may be combined into many other different systems or applications. Various components may be implemented in hardware or software or embedded software. Various presently unforeseen or unanticipated alternatives, modifications, variations or improvements may be made by those skilled in the art, each of which is also intended to be encompassed by the disclosed embodiments.

Terminology that is relevant to the disclosure provided above includes:

A "robotic device" or "robot" refers to an electronic device that includes a processor, programming instructions, and one or more components that based on commands from the processor can perform at least some operations or tasks with minimal or no human intervention. For example, a robotic device may perform one or more automatic functions or function sets. Examples of such operations, functions or tasks may include without, limitation, surgical tasks, registration of points to images, task planning, and/or the like. Example automated devices may include, without limitation, surgical tools, registration tools, surgical robots or components thereof, a vision system, sensors (e.g., force sensors) or the like.

An "electronic device" or a "computing device" refers to a device that includes a processor and memory. Each device may have its own processor and/or memory, or the processor and/or memory may be shared with other devices as in a virtual machine or container arrangement. The memory will contain or receive programming instructions that, when executed by the processor, cause the electronic device to perform one or more operations according to the programming instructions.

The terms "memory," "memory device," "data store," "data storage facility", "computer readable medium" and the like each refer to a non-transitory device on which computer-readable data, programming instructions or both are stored. Except where specifically stated otherwise, the terms "memory," "memory device," "data store," "data storage facility" and the like are intended to include single device embodiments, embodiments in which multiple memory devices together or collectively store a set of data or instructions, as well as individual sectors within such devices.

The terms "processor" and "processing device" refer to a hardware component of an electronic device that is configured to execute programming instructions. Except where specifically stated otherwise, the singular term "processor" or "processing device" is intended to include both single-processing device embodiments and embodiments in which multiple processing devices together or collectively perform a process.

In this document, the terms "communication link" and "communication path" mean a wired or wireless path via which a first device sends communication signals to and/or receives communication signals from one or more other devices. Devices are "communicatively connected" if the devices are able to send and/or receive data via a communication link. "Electronic communication" refers to the transmission of data via one or more signals between two or more electronic devices, whether through a wired or wireless network, and whether directly or indirectly via one or more intermediary devices.

The term "surgical task" or "task" refers to one or more steps that are performed using a surgical tool for manipulation or modification of a patient tissue.

In this document, when relative terms of order such as "first" and "second" are used to modify a noun, such use is simply intended to distinguish one item from another, and is not intended to require a sequential order unless specifically stated.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

In addition, terms of relative position such as "vertical" and "horizontal", or "front" and "rear", when used, are intended to be relative to each other and need not be absolute, and only refer to one possible position of the device associated with those terms depending on the device's orientation.

It will be apparent to those skilled in the art that various modifications/variations can be made to the disclosed systems and methods and can be applied to other areas such as non-surgical workmanship (e.g. carpentry) and animal surgery. The disclosed specification and examples are exemplary only.

The invention claimed is:

1. A method for controlling a robotic device to perform a tissue modification task, the method comprising, by a processor:

performing a coarse registration, wherein a user positions and orients a camera of a vision system and a registration tool tip of a surgical tool when in contact with tissue such that a real-time image of the tissue as captured by the camera is roughly aligned to a reference image of a contacted tissue;

identifying, using the robotic device in a hand-guidance mode, a plurality of registration points on a tissue surface, and mapping the plurality of registration points to a patient's image data; and transforming a task plan relative to the patient's image data to a second coordinate frame of the robotic device;

controlling, using the task plan, the robotic device to autonomously or semi-autonomously execute a tissue modification task by:

incrementally moving the surgical tool from a pre-entry position towards an entry point, measuring force applicable on the surgical tool at each incremental position until the surgical tool reaches a first datum point, identifying the first datum point as an entry point of the surgical tool into the tissue, where a force applicable on the surgical tool at the first datum point is greater than a first threshold value, activating, while being positioned at the first datum point, the surgical tool to perform the tissue modification task along a planned trajectory, determining, based on at least the force measurements on the surgical tool or a position of the tool along the planned trajectory, whether the surgical tool has reached an end of the planned trajectory, in response to determining that the surgical tool has reached the end of the planned trajectory, retracting the surgical tool from the tissue.

2. The method of claim 1, further comprising displaying, on a display device, a position of the surgical tool in relation to the patient's image data and the planned trajectory in real-time.

3. The method of claim 1, further comprising controlling the robotic device to position the surgical tool at the pre-entry position that is within a threshold distance of the entry point and at an angle of entry into the tissue.

4. The method of claim 1, further comprising continuously monitoring a force applicable on the surgical tool while performing the tissue modification task by subtracting a reference force from a measured force, the reference force comprising a gravitation force.

5. The method of claim 4, further comprising, upon activation of the surgical tool:

controlling the robotic device to position the surgical tool at a first incremental position along the planned trajectory to perform the tissue modification task;

determining, at the first incremental position, whether the force applicable has become less than a second threshold value; and in response to determining that the force applicable has become less than the second threshold value, controlling the robotic device to position the surgical tool at a second incremental position along the planned trajectory to perform the tissue modification task.

6. The method of claim 5, further comprising, in response to determining that the force applicable has not become less than the second threshold value, continuing the monitoring of the force applicable on the surgical tool while performing the tissue modification task until expiration of a first time period indicative of a risk.

7. The method of claim 6, further comprising transmitting an alert to a user when the force applicable exceeds a third threshold value.

8. The method of claim 7, further comprising determining the first threshold value, the second threshold value, and the third threshold value based on at least an estimated stiffness of the tissue.

9. The method of claim 1, further comprising controlling the robotic device to abort the tissue modification task in response to determining that a search limit has been exceeded prior to identification of the first datum point, the search limit comprising at least one of the following: a time, a distance, or a number of attempts.

10. The method of claim 1, wherein identifying the plurality of registration points on the tissue surface comprises:

attaching a registration tool to the robotic device;

monitoring applicable force on the registration tool while the registration tool is contacted with a plurality of points over the tissue surface in the hand-guidance mode comprising subtracting a reference force from a measured force, the reference force comprising a gravitation force; and identifying one or more positions of the registration tool as registration points when the monitored applicable force is greater than a contact threshold value.

11. The method of claim 10, further comprising performing, using one or more of the plurality of registration points, segmentation of three-dimensional surface information of the tissue collected by a vision system to identify a second plurality of registration points proximate to the one or more of the plurality of registration points.

12. The method of claim 1 further comprising receiving the task plan, relative to the patient's image data, the task plan comprising information relating to the entry point of the surgical tool into the tissue and the planned trajectory of the surgical tool inside the tissue for performing the tissue modification task;

determining a spatial relationship between a first coordinate frame of the task plan and the second coordinate frame of the robotic device.

13. The method of claim 2, wherein receiving the task plan comprises receiving the task plan from a user by user-guided contact of the surgical tool with a patient's anatomy and at least one user-specified plan parameter.

14. A system for controlling a robotic device to perform a tissue modification task, the system comprising a robotic device comprising a surgical tool; a processor; and a non-transitory computer readable medium comprising one or more programming instructions that when executed by the processor will cause the processor to:

perform a coarse registration, wherein a coarse registration step comprises a user positioning and orienting a camera of a vision system and registration tool tip when in contact with an anatomy such that a real-time image of the anatomy as captured by the camera is roughly aligned to a reference image of the contacted anatomy, identify, using the robotic device in a hand-guidance mode, a plurality of registration points on the tissue surface, and map the plurality of registration points to a patient's image data; and transform the task plan relative to the patient's image data to a second coordinate frame of the robotic device;

control, using the task plan, the robotic device to autonomously or semi-autonomously execute the tissue modification task by:

incrementally moving the surgical tool from a pre-entry position towards the entry point until the surgical tool reaches a first datum point; and, measuring force applicable on the surgical tool at each incremental position until the surgical tool reaches the first datum point, identifying the first datum point as the entry point of the surgical tool into the tissue, where a force applicable on the surgical tool at the first datum point is greater than a first threshold value, activating, while being positioned at the first datum point, the surgical tool to perform the tissue modification task along a planned trajectory, determining, based on force measurements on the surgical tool or a position of the tool along the planned trajectory, whether the surgical tool has reached an end of the planned trajectory, in response to determining that the surgical tool has reached the end of the planned trajectory, retracting the surgical tool from the tissue.

15. The system of claim 14, further comprising programming instructions that when executed by the processor will cause the processor to display, on a display device, a position of the surgical tool in relation to the patient's image data and the planned trajectory in real-time.

16. The system of claim 14, further comprising programming instructions that when executed by the processor will cause the processor to control the robotic device to execute the tissue modification task by positioning the surgical tool at the pre-entry position that is within a threshold distance of the entry point and at an angle of entry into the tissue.

17. The system of claim 14, further comprising programming instructions that when executed by the processor will cause the processor to continuously monitor a force applicable on the surgical tool while performing the tissue modification task by subtracting a reference force from a measured force, the reference force comprising a gravitation force.

18. The system of claim 17, further comprising programming instructions that when executed by the processor will cause the processor to, upon activation of the surgical tool:

control the robotic device to position the surgical tool at a first incremental position along the planned trajectory to perform the tissue modification task;

determine, at the first incremental position, whether the force applicable has become less than a second threshold value; and in response to determining that the force applicable has become less than the second threshold value, control the robotic device to position the surgical tool at a second incremental position along the planned trajectory to perform the tissue modification task.

19. The system of claim 18, further comprising programming instructions that when executed by the processor will cause the processor to, in response to determining that the force applicable has not become less than the second threshold value, continue the monitoring of the force applicable on the surgical tool while performing the tissue modification task until expiration of a first time period indicative of a risk.

20. The system of claim 19, further comprising further comprising programming instructions that when executed by the processor will cause the processor to transmit an alert to a user when the force applicable exceeds a third threshold value.

21. The system of claim 20, further comprising further comprising programming instructions that when executed by the processor will cause the processor to determine the first threshold value, the second threshold value, and the third threshold value based on at least an estimated stiffness of the tissue.

22. The system of claim 14, further comprising further comprising programming instructions that when executed by the processor will cause the processor to control the robotic device to abort the tissue modification task in respond to determining that a search limit has been exceeded prior to identification of the datum point, the search limit comprising at least one of the following: a time, a distance, or a number of attempts.

23. The system of claim 14, wherein the programming instructions that when executed by the processor will cause the processor to identify the plurality of registration points on the tissue surface comprise programming instructions that when executed by the processor will cause the processor to:

attach a registration tool to the robotic device;

monitor applicable force on the registration tool while the registration tool is contacted with a plurality of points over the tissue surface in the hand-guidance mode and subtract a reference force from a measured force, the reference force comprising a gravitation force; and identify one or more positions of the registration tool as registration points when the monitored applicable force is greater than a contact threshold value.

24. The system of claim 23, further comprising programming instructions that when executed by the processor will cause the processor to perform, using one or more of the plurality of registration points, segmentation of three-dimensional surface information a camera image of the tissue collected by a vision system to identify a second plurality of registration points proximate to the one or more of the plurality of registration points.

25. The system of claim 14, wherein the programming instructions that when executed by the processor will cause the processor to receive the task plan comprise programming instructions that when executed by the processor will cause the processor to receive the task plan from a user by user-guided contact of the surgical tool with a patient's anatomy and at least one user-specified plan parameter.

26. The system of claim 14, further comprising programming instructions that when executed by the processor will cause the processor to receive the task plan, relative to a patient's image data, the task plan comprising information relating to an entry point of the surgical tool into a tissue and a planned trajectory of the surgical tool inside the tissue for performing the tissue modification task, and determine a spatial relationship between a first coordinate frame of a task plan and a second coordinate frame of the robotic device.

27. A method for controlling a robotic device to perform a tissue modification task, the method comprising, by a processor:

receiving a task plan, relative to a patient's image data, the task plan comprising information relating to an entry point of a surgical tool into a tissue and a planned trajectory of the surgical tool inside the tissue for performing the tissue modification task;

determining a spatial relationship between a first coordinate frame of a task plan and a second coordinate frame of the robotic device by:

performing a coarse registration step, wherein a user positions and orients a camera of a vision system and a registration tool tip when in contact with the tissue such that a real-time image of the tissue as captured by the camera is roughly aligned to a reference image of the contacted tissue;

identifying, using the robotic device in a hand-guidance mode, a plurality of registration points on a tissue surface, and mapping the plurality of registration points to a patient's image data; and transforming the task plan relative to the patient's image data to the second coordinate frame of the robotic device;

controlling, using the task plan, the robotic device to autonomously or semi-autonomously execute the tissue modification task by:

incrementally moving the surgical tool from a pre-entry position towards the entry point, measuring force applicable on the surgical tool at each incremental position until the surgical tool reaches a first datum point, identifying the first datum point as the entry point of the surgical tool into the tissue, where a force applicable on the surgical tool at the first datum point is greater than a first threshold value, activating, while being positioned at the first datum point, the surgical tool to perform the tissue modification task along the planned trajectory, determining, based on at least the force measurements on the surgical tool or a position of the tool along the planned trajectory, whether the surgical tool has reached an end of the planned trajectory, in response to determining that the surgical tool has reached the end of the planned trajectory, retracting the surgical tool from the tissue.

28. A system for controlling a robotic device to perform a tissue modification task, the system comprising a robotic device comprising a surgical tool;

a processor; and a non-transitory computer readable medium comprising one or more programming instructions that when executed by the processor will cause the processor to:

receive a task plan, relative to a patient's image data, the task plan comprising information relating to an entry point of the surgical tool into a tissue and a planned trajectory of the surgical tool inside the tissue for performing the tissue modification task;

determine a spatial relationship between a first coordinate frame of a task plan and a second coordinate frame of the robotic device wherein determining the spatial relationship further comprises programming instructions that when executed by the processor cause the processor to;

perform a coarse registration, wherein a coarse registration step comprises a user positioning and orienting a camera of a vision system and registration tool tip when in contact with an anatomy such that a real-time image of the anatomy as captured by the camera is roughly aligned to a reference image of the contacted anatomy;

identify, using the robotic device in a hand-guidance mode, a plurality of registration points on the tissue surface, and map the plurality of registration points to a patient's image data; and transform the task plan relative to the patient's image data to the second coordinate frame of the robotic device;

control, using the task plan, the robotic device to autonomously or semi-autonomously execute the tissue modification task by:

incrementally moving the surgical tool from a pre-entry position towards the entry point until the surgical tool reaches a first datum point; and, measuring force applicable on the surgical tool at each incremental position until the surgical tool reaches the first datum point, identifying the first datum point as the entry point of the surgical tool into the tissue, where a force applicable on the surgical tool at the first datum point is greater than a first threshold value, activating, while being positioned at the first datum point, the surgical tool to perform the tissue modification task along the planned trajectory, determining, based on force measurements on the surgical tool or a position of the tool along the planned trajectory, whether the surgical tool has reached an end of the planned trajectory, in response to determining that the surgical tool has reached the end of the planned trajectory, retracting the surgical tool from the tissue.

* * * * *